(12) United States Patent
Thevelein et al.

(10) Patent No.: US 9,809,830 B2
(45) Date of Patent: Nov. 7, 2017

(54) MUTANT NNK1 ALLELE AND ITS USE

(71) Applicants: VIB VZW, Ghent (BE); KATHOLIEKE UNIVERSITEIT LEUVEN, K.U. LEUVEN R&D, Leuven (BE)

(72) Inventors: Johan Thevelein, Blanden (BE); Mekonnen Demeke, Leuven (BE); Maria Remedios Foulquié Moreno, Brussels (BE)

(73) Assignees: VIB VZW, Ghent (BE); KATHOLIEKE UNIVERSITEIT LEUVEN, K.U. LEUVEN R&D, Leuven (BE)

( * ) Notice: Subject to any disclaimer, the term of this patent is extended or adjusted under 35 U.S.C. 154(b) by 0 days.

(21) Appl. No.: 15/103,916

(22) PCT Filed: Dec. 12, 2014

(86) PCT No.: PCT/EP2014/077528
§ 371 (c)(1),
(2) Date: Jun. 13, 2016

(87) PCT Pub. No.: WO2015/086805
PCT Pub. Date: Jun. 18, 2015

(65) Prior Publication Data
US 2016/0312244 A1    Oct. 27, 2016

(30) Foreign Application Priority Data
Dec. 13, 2013  (EP) ..................................... 13197206

(51) Int. Cl.
*C12P 7/06* (2006.01)
*C12N 1/14* (2006.01)
*C12N 9/12* (2006.01)
*C12P 7/10* (2006.01)

(52) U.S. Cl.
CPC .................. *C12P 7/06* (2013.01); *C12N 9/12* (2013.01); *C12P 7/10* (2013.01); *C12Y 207/11001* (2013.01); *Y02E 50/16* (2013.01); *Y02E 50/17* (2013.01)

(58) Field of Classification Search
CPC ........ Y02E 50/17; C12N 9/1205; C12N 15/81
USPC ...................... 435/161, 254.2, 194
See application file for complete search history.

(56) References Cited

PUBLICATIONS

Wisselink H Wouter et al., "Novel Evolutionary Engineering Approach for Accelerated Utilization of Glucose, Xylose, and Arabinose Mixtures by Engineered *Saccharomyces cerevisiae* Strains", Applied and Environmental Microbiology, American Society for Microbiology, pp. 907-914, vol. 75, No. 4 (Feb. 2009).
Breitkreutz Ashton et al., "A global protein kinase and phosphatase interaction network in yeast", Science, pp. 1043-1046, vol. 328, No. 5981 (May 2010).
Database UniProt, "RecName: Full=Nitrogen network kinase 1" XP002737622, (Jun. 1994).

*Primary Examiner* — Tekchand Saidha
(74) *Attorney, Agent, or Firm* — Browdy and Neimark, PLLC

(57) ABSTRACT

The present invention relates to a mutant NNK1 allele, especially a mutant carrying a mutation at position of amino acid 807 of the wild type sequence. The invention relates further to the use of said mutant allele to increase the fermentation rate in yeast, preferably in *Saccharomyces*. The mutant allele is especially useful to increase the xylose to ethanol fermentation rate.

18 Claims, 7 Drawing Sheets

MUTANT NNK1 ALLELE AND ITS USE

The present invention relates to a mutant NNK1 allele, especially a mutant carrying a mutation at position of amino acid 807 of the wild type sequence. The invention relates further to the use of said mutant allele to increase the fermentation rate in yeast, preferably in *Saccharomyces*. The mutant allele is especially useful to increase the xylose to ethanol fermentation rate.

In the past few decades, substantial efforts have been focused on production of bioethanol from non-food biomass such as agricultural and forest residues, energy crops, and waste streams. Such feedstocks are composed of cellulose, hemicellulose and lignin (collectively termed lignocelluloses). Bio-ethanol production from such lignocellulosic biomass is considered to be one of the most sustainable and environmental-friendly alternative fuel productions for the transport sector. After decades of research on improvement of bioethanol production from such biomass, economically viable production remains a great challenge. Lack of yeast strains that ferment all the sugars in the lignocellulosic biomass under industrial condition is among the major obstacles in the commercialization of bioethanol production from lignocellulosic biomass.

The yeast *Saccharomyces cerevisiae* is the best organism for industrial ethanol production owing to its high rate of fermentation of hexose sugars, high tolerance to ethanol, inhibitors, acidity and other industrial process conditions, well-established production, storage and transport systems at commercial scale, comprehensive physiological and molecular knowledge, and its genetic tractability. However, it is unable to metabolize pentose sugars, particularly D-xylose, which represent up to 35% of total sugars in lignocellulosic feedstocks. Thus, efficient utilization of D-xylose is required for cost effective and sustainable production of ethanol from lignocellulosic material.

Considerable progress has been made in the past few years in the development of yeast strains that are able to ferment D-xylose through heterologous expression of D-xylose metabolism pathways from natural D-xylose utilizing yeasts or bacteria into *S. cerevisiae*. However, expression of all the genes known to be essential for D-xylose fermentation alone in *S. cerevisiae* has never resulted in efficient D-xylose fermentation capacity, especially in industrial strains. As a result, metabolic engineering strategies are frequently combined with random strain modification techniques, such as mutagenesis, genome shuffling and evolutionary adaptation (Kuyper et al., 2005; Wisselink et al., 2009). This indicates that, in addition to expression of the well-known genes (genes coding of xylose isomerase or xylose reductase and xylitol Dehydrogenase; xylulokinase, and the 4 genes of the non-oxidative pentose phosphate pathway), other genes or genetic modifications are important for rapid D-xylose utilization capacity in *S. cerevisiae*. Moreover, since pentose fermentation appears to be much more sensitive to the toxic inhibitors, the productivity of the yeast in high-density lignocellulose hydrolysates is largely determined by the strain's robustness during pentose fermentation. As a result, laboratory strains do not meet the industrial standards, in particular the demand for high yield and productivity in non-detoxified lignocellulosic hydrolysates.

To address these obstacles, we have developed a robust industrial strain (GS1.11-26) that is able to efficiently utilize D-xylose with a yield of ethanol from D-xylose that was higher than the yield obtained by any reported recombinant strain of *S. cerevisiae* (Demeke et al., 2013). GS1.11-26 has been constructed from one of the most widely used first generation bioethanol production yeast strains (Ethanol Red), in to which the a *Clostridium phytofermentans* xylA based D-xylose and an L-arabinose gene cassette has been inserted. Despite the presence of all known genes required for D-xylose and arabinose utilization in the genome, the original recombinant industrial strain was unable to utilize D-xylose or L-arabinose. GS1.11-26 was developed from this recombinant strain using a systematic evolutionary engineering approach that includes random mutagenesis, genome shuffling followed by selection in a D-xylose-enriched lignocellulose hydrolysate, and adaptive evolution in D-xylose.

To identify the genetic factors responsible for the rapid D-xylose utilization in GS1.11-26, we performed a quantitative trait loci (QTL) mapping using a modified pooled segregant whole genome sequence analysis (PSS). This resulted in the identification of at least three genomic loci that are linked to the fast D-xylose fermentation rate in GS1.11-26. One of the QTL (QTL1) was linked to the gene cassette that has been inserted in the original recombinant strain. We then evaluated of the second QTL (QTL2) by reciprocal hemizygosity analysis. Surprisingly, we found in this QTL a mutation in the gene NNK1 that improves the rate of D-xylose utilization in GS1.11-26. NNK1 hadn't been associated previously with D-xylose metabolism, but the mutation is clearly increasing the xylose fermentation rate.

A first aspect of the invention is a mutant NNK1 allele, encoding a protein carrying a mutation at position 807 of the reference sequence SEQ ID No. 2. The protein encoded by the allele may carry other mutations when compared to this reference sequence, as it is known that some genetic variability may occur from strain to strain; preferably, the protein encoded by said mutant allele shows 80% identity, more preferably 85% identity, more preferably 90% identity, more preferably 95% identity, most preferably 99% identity with the reference sequence as measured over the full length of the sequence using BLASTp (Altschul et al., 1997). Preferably, the protein encoded by said mutant allele retains its protein kinase activity. Preferably, the mutation according to the invention, in the Nnk1p is a serine by arginine replacement. Preferably, the mutant allele is encoding a protein as represented by SEQ ID No. 4. Even more preferably, the mutant allele comprises a sequence as represented by SEQ ID No. 3.

Another aspect of the invention is the use of a mutant according to the invention to increase the fermentation rate in yeast. Yeast, as used here, can be any yeast useful for ethanol production, including, but not limited to *Saccharomyces*, *Zygosaccharomyces*, *Brettanomyces* and *Kluyveromyces*. Preferably, said yeast is a *Saccharomyces* sp., even more preferably it is a *Saccharomyces cerevisiae* sp. The "fermentation rate", as used here, is the amount of is the amount of carbohydrate transformed into ethanol per unit of time; it might be measured as $CO_2$ produced per unit of time. "Increase" as used here, means that the fermentation rate of the strain carrying the mutant allele is higher than the fermentation rate of an isogenic strain without the mutant allele, when the fermentation is carried out under the same conditions. Preferably, said carbohydrate is xylose. In one preferred embodiment, "the use" as used here, is the replacement of one or more endogenous NNK1 alleles by one or more mutant alleles according to the invention. In another preferred embodiment "the use" as used here, is the overexpression of a mutant NNK1 allele.

Another aspect of the invention is a method to increase the fermentation rate of yeast, comprising the replacement of a wild type NNK1 allele by a mutant NNK1 allele according to the invention. Still another aspect of the invention is a method to increase the fermentation rate of a yeast, comprising the transformation of said yeast using a construct allowing the overexpression of a mutant NNK1 allele according to the invention. Methods for overexpression are known to the person skilled in the art, as a non-limiting example, said construct may be an integrative construct, wherein the NNK1 allele is placed under control of a strong promoter, or it may be a multicopy construct, either integrative or self-replicating. Preferably, said yeast is a *Saccharomyces* sp. Preferably, said fermentation rate is the fermentation rate on xylose.

Still another aspect of the invention is a xylose fermenting yeast, carrying at least one mutant NNK1 allele according to the invention. Preferably, said xylose fermenting yeast is a transgenic *Saccharomyces* sp., carrying a xylose isomerase of another organism, such as, but not limited to the xylose isomerase of *Clostridium phytofermentans*. Preferably, said strain is not *Saccharomyces cerevisiae* GS1.11-26. Preferably, there is at least one copy of the mutant allele according to the invention per haploid genome, even more preferably, there is more than one copy of the mutant allele according to the invention per haploid genome. Preferably, the mutant NNK1 allele is introduced in the strain by recombinant DNA technology, such as, but not limited to gene replacement or site directed mutagenesis.

EXAMPLES

Materials and Methods to the Examples

Strains and Growth Conditions

Figures 1, 2:
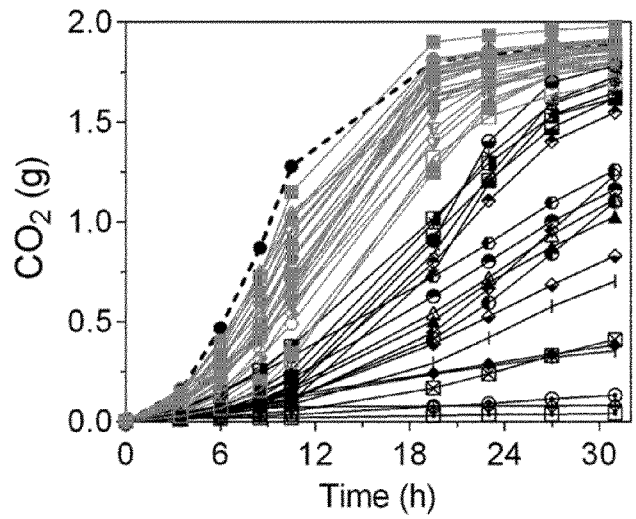
FIG. 1. D-xylose fermentation profile of the 48 preselected D-xylose utilizing segregants obtained from the tetraploid strain GS1.11-26/Fseg25, in YP medium containing 40 g/L D-xylose. The 27 selected segregants with the best performance are shown in grey lines and the parent strain GS1.11-26 is shown broken lines. A similar fermentation profile was obtained during the preselection step in the same conditions.
FIG. 2. SNP inheritance and possible SNP variant frequency in diploid segregants obtained from tetraploid parent. Each sequence in the upper box represents a region of a chromosome with nucleotide polymorphisms indicated in red. Nucleotides in grey, in a box or in a circle are the same as in the reference strain. A box is used for nucleotides that originate from Fseg25, while a circle is used for nucleotides from GS1.11-26. The 6 possible genotypes are listed and numbered from 1 to 6. The Mendelian random segregation with only bivalent pairing was used for calculation. The lower left box shows the possible segregation of a region with a homozygous SNP nucleotide (G in red). In case 1 with random segregation, the SNP variant frequency in the segregants will be 0.5 (6 G and 6 T). In case 2, when the homozygous SNP nucleotide (G in black) is linked to the phenotype, the SNP frequency in the inferior pool will be less than 0.5 (close to 0) since the segregants will mostly contain the wild type allele T (genotype number 6). The SNP variant frequency in the superior pool will be higher than 0.6, since all the segregants should contain this SNP nucleotide (G in black, genotypes 1 to 5). In this case, the SNP variant frequency varies depending on the type of mutation (dominant or recessive). The lower right box shows the possible frequency of a heterozygous SNP nucleotide in segregants. During random segregation (case 1), the SNP variant frequency will be 0.25 (3/12). When the SNP nucleotide is important for the phenotype (case 2), the SNP frequency will be much lower than 0.5 (close to 0), since most of the segregants should have the genotype 4, 5 or 6, which do not carry the SNP nucleotide (T in black), The superior segregants should carry the SNP nucleotide (genotype 1, 2 and 3), which results in the frequency of 0.5.

The *S. cerevisiae* strains utilized in this study are listed in Table 1. Yeast cells were propagated in yeast extract peptone (YP) medium (10 g/L yeast extract, 20 g/L bacteriological peptone) supplemented with either 20 g/L D-xylose (YPX) or 20 g/L D-glucose (YPD). For solid plates, 15 g/L Bacto agar was added. For batch fermentation, either YP medium or synthetic complete medium (1.7 g/L Difco yeast nitrogen base without amino acid and without ammonium sulfate, 5 g/L ammonium sulfate, 740 mg/L CSM-Trp and 100 mg/L L-tryptophan) supplemented with D-xylose or D-glucose/D-xylose mixture was used. For selection of strains expressing the KanMX resistance marker, 200 mg/L geneticin was added to the medium. Yeast strains were maintained at −80° C. in stock medium composed of YP and 26% glycerol.

TABLE 1

*S. cerevisiae* strains used in the study.

| Yeast strain | Main characteristics | Source/reference |
|---|---|---|
| Ethanol Red | Industrial bioethanol production strain, MATa/α | Fermentis, a division of S. I. Lesaffre, Lille, France |
| HDY.GUF5 | Ethanol Red; pyk2::XylA; XKS1; TAL1; TKL1; RPE1; RKI1; HXT7; AraT; AraA; AraB; AraD; TAL2; TKL2 | Goethe University of Frankfurt, Germany |
| M315 | HDY.GUF5 + 3 h mutagenesis in 3% EMS, MATα/α | This study |
| GS1.11-26 | HDY.GUF5, M315 and M492 + genome shuffling and evolutionary adaptation, MATα/α | This study |
| Fseg25 | Segregant of JT21653b selected for high inhibitor tolerance in spruce hydrolysate fermentation, MATa/a | This study |
| MV1000 | Mating type tester strain, MATa, bar1Δ | MCB KU Leuven |
| MV1000 | Mating type tester strain, MATα, sst2Δ | MCB KU Leuven |

Screening for D-xylose Fermentation Capacity

We first performed a prescreening of the 819 segregants based on their ability to grow on agar plate with D-xylose as a carbon source (YPX), in order to reduce the number of strains to be evaluated in fermentations. All segregants that showed detectable growth on YPX were further analyzed for growth in liquid YPX medium. For that purpose, the strains were inoculated in 1 ml YPX medium at an initial OD$_{600}$ of 1.0. After about 24 h of incubation, a range of cell densities, from $OD_{600}$ of about 5 up to 33 was observed for the different segregants. Strain GS1.11-26 showed an $OD_{600}$ between 28 and 33 in different replicate growth assays. To monitor the correlation between growth in liquid YPX and fermentation performance, segregants growing to an $OD_{600}$ above 5 were evaluated by fermentation in YP medium containing 40 g/L D-xylose. We observed that, most of the best D-xylose fermenting strains also performed well in such growth evaluation experiments. Thus, the majority of poor D-xylose fermenting segregants could be excluded by using a cut-off value for growth to an $OD_{600}$ of 15 in 24 h, since all the good D-xylose fermenting segregants grew to an $OD_{600}$ of above 15. Hence, growth in liquid YPX medium for 24 h and selection of the segregants growing to a minimum $OD_{600}$ of 15 was considered to be the best method for rapid initial screening and elimination of poor performers.

Using this method, about 168 segregants growing to $OD_{600}$ values of about 15 in 24 h were preselected and further tested for D-xylose fermentation performance in semi-anaerobic conditions. This was done in different batches of experiments and finally resulted in 48 segregants with moderate to rapid D-xylose fermentation capacity. To allow a proper comparison, the 48 selected segregants were evaluated in a single batch of fermentation experiments. The 27 best segregants, with a D-xylose fermentation performance close to that of GS1.11-26, were eventually selected for further analysis.

Determination of Mating Type by PCR and Pheromone Assay

The determination of the mating type was done by PCR and pheromone assay. PCR was performed with a primer for the MAT locus and a MATa or MATα specific primer (Huxley et al., 1990). To validate mating type by a pheromone assay, two tester strains of *S. cerevisiae*, MATa bar1-Δ, and MATα sst2-Δ, were used. A small amount of tester strain was mixed with 1% agar at 50° C. and immediately poured on top of a YPD plate. After the top agar solidified, about 10 μL of cell suspension from strains to be tested was spotted onto each tester plate. The cell suspension was prepared by mixing a small amount of cells from a plate in sterile milli-Q water. After 24 h incubation at 30° C., MATα cells showed a zone of growth inhibition (halo) on plates of the bar1-Δ, strain while MATa cells showed a zone of growth inhibition on plates of the sst2-Δ strain. Diploid cells did not produce a zone of inhibition since they do not produce either of the pheromones.

Molecular Biology Methods

Yeast cells were transformed with the LiAc/SS-DNA/PEG method (Gietz et al., 1995) or electroporation modified from Thompson et al., (1998). Genomic DNA from yeast was extracted with PCI [phenol/chloroform/isoamyl-alcohol (25:24:1)] method (Hoffman and Winston, 1987). PCR was performed with Phusion DNA polymerase (New England Biolabs) for construction of the vectors and sequencing purposes, and ExTaq (Takara) for diagnostic purposes. Sanger sequencing was performed by the Genetic Service Facility of the VIB, Belgium.

Plasmid Construction

Cloning was performed using the standard restriction and ligation protocol as described in Sambrook et al., (1989). About 1 to 2 μg DNA was digested with the specific restriction enzyme supplied by New England Biolabs, for 2 to 3 h at the recommended temperature. Dephosphorylation of the digested vector was performed using FastAP kit from Fermentas life Sciences. Ligation was performed using T4 DNA ligase (Promega) according to the manufacturer's recommendation. *E. coli* cells were transformed using the $CaCl_2$ method (Sambrook et al., 1989). Plasmids were propagated in *E. coli* strain TOP10 (Invitrogen), grown in LB medium containing 100 μg/mL ampicillin at 37° C.

Genomic DNA Isolation and Pooled Segregant Whole Genome Sequencing

All the segregants selected for sequencing were grown in 5 mL YPD for 2 days at 30° C. Equal amount of cells from each segregants were pooled based on optical density measurement. The genomic DNA from the pools of segregants and from each parent strain was extracted using the standard protocol described in Johnston (1994). About 6 μg high quality DNA samples were sent for sequencing to BGI HONG KONG CO.,LIMITED (Hong Kong). Paired end sequencing was conducted using high-throughput Illumina sequencing technology. A paired end sequence library of 500 bp was constructed and sequence reads of 90 bp were generated. Average sequence coverage of about 40× was achieved for both strains. The sequencing reads provided from BGI were aligned onto the reference S288c genome sequence using CLC Genomics Workbench5 or Lasergene's SeqMan Pro software (DNASTAR). The sequencing depth was calculated based on the alignment.

Determination of Ploidy by Flow Cytometry.

Flow cytometric analysis of DNA content was performed according to Popolo et al., (1982). Briefly, exponentially growing cells were washed with ice-cold sterile water and fixed with 70% ethanol. Cells were treated with RNase (1 mg/mL) and the DNA was stained with propidium iodide (0.046 M) in 50 mM Tris, pH 7.7 and 15 mM $MgCl_2$, at 4° C. for about 48 h. The fluorescence intensity was measured using a FACScan instrument (Becton Dickinson)

Reciprocal-hemizygosity Analysis (RHA)

RHA was performed according to Steinmetz et al., (2002), in a diploid strain background that carried heterozygous allele for the specific gene of interest. To perform the gene deletions, the KanMX cassette was first amplified from the vector pJET 1,2 B-kanMx-P using primers that contain about 60 by extra sequences that are homologous to upstream (in the forward primer) and downstream (in the reverse primer) of the gene to be deleted. The PCR product was purified from agarose gel using Wizard® SV Gel and PCR Clean-Up System (Promega) and transformed into the yeast strain. The correct integration of the marker was evaluated by PCR, and the region was subsequently sequenced to confirm the deletion of either of the allele. Two isogenic strains that carry either the mutant or the wild type allele were selected for evaluation.

Determination of Specific D-xylose isomerase Activity

The specific activity of D-xylose isomerase was measured based on the isomerization of D-xylose to xylulose, followed by reduction of xylulose to xylitol by sorbitol Dehydrogenase (Kersters-Hilderson et al., 1987). Cell extraction was performed by disruption of cells with glass beads in 20 mM Tris HCl, pH 8, using a Fast Prep homogenizer. Protein concentration was determined using the Pierce 660 nm Protein Assay kit (Thermo Scientific) according to the manufacturer's manual. XI activity in the fresh cell extract was determined at 30° C. The assay mixture contained 100 mM Tris-HCl buffer (pH 7.5), 10 mM $MgCl_2$, 0.15 mM NADH and 2U sorbitol dehydrogenase. The reaction was started by addition of D-xylose to a final concentration of 500 mM. A molar extinction coefficient of 6.25 $(mM\ cm)^{-1}$ at 340 nm for NADH was used to calculate specific activity. Specific activity was expressed as Units per mg protein. One unit corresponds to the conversion of 1 µM of substrate into product in one minute under the specified reaction conditions.

Small-scale Fermentations

Semi-anaerobic sequential batch fermentations were performed in 100 mL YP medium containing 40 to 100 g/L D-xylose as sole carbon source, in cylindrical tubes with cotton plugged rubber stopper. Cultures were continuously stirred magnetically at 120 rpm and incubated at 35° C. The weight of the fermentation tubes was measured every few hours. The fermentation profile was estimated from weight loss due to $CO_2$ release during fermentation.

Cell Mass Concentration

Optical Density ($OD_{600nm}$) was used to estimate cell dry weight (DW). The DW for inoculums was measured by filtering a 10 mL culture aliquot of a known $OD_{600}$ value in pre-weighed 0.2 mm Supor Membrane disc filters (PALL Corporation, USA), washing the filter with MilliQ water, and drying it in a microwave oven at about 150 watt for 15-20 min to constant weight. The correlation between dry weight and $OD_{600}$ was measured for each strain tested.

Example 1

Comparison of the Xylose Fermentation Capacity of Segregants

In this study, we have used a modified method of PSS for identification of genetic loci responsible for the high D-xylose fermentation rate in the diploid strain GS1.11-26. One of the limitations of the regular PSS described in Swinnen et al., 2012a is the requirement for haploid strains of opposite mating type as the starting parent strains. Most industrial yeast strains are diploid, polyploid or aneuploid. Obtaining a stable haploid derivative from such industrial strains displaying the trait of interest that is as good as the parent strain, is a strong challenge, if not impossible (Swinnen et al., 2012b). Unlike the regular PSS, we have started the mapping with the D-xylose fermenting MATα/α diploid strain GS1.11-26 (also aneuploid, with three copies of two sets of its chromosomes) as the superior starting strain. This strain was crossed with a diploid MATa/a strain of a genetically unrelated baker's yeast Fseg25 that does not ferment xylose. Fseg25 also has three copies of two sets of chromosomes. We then screened 819 segregants from the tetraploid hybrid strain, and subsequently selected 27 diploid segregants that ferment D-xylose at a rate close to GS1.11-26 (FIG. 1).

Flow cytometry analysis showed that the selected 27 segregants all had a DNA content similar to that of a diploid control strain. Hence, all segregants appeared to be diploid strains, although aneuploidy for one or more chromosomes cannot be ruled out.

Example 2

Whole Genome Sequencing

The pooled genomic DNA of the 27 best D-xylose fermenting segregants, a control pool of 27 segregants that do not ferment D-xylose but showed growth on solid medium with xylose, and the genomic DNA of the inferior parent Fseg25 and the superior parent GS1.11-26 were sequenced using high-throughput Illumina sequencing technology (BGI, China). Paired end sequencing was conducted with a 500 bp library. To ensure selection of high quality sequence reads, the raw data were filtered for several parameters including removal of adaptor contamination and low quality reads (Table 2). We received the resulting high quality reads for further bioinformatics analysis.

TABLE 2

Statistics of the Illumina sequence reads before and after quality filtering. "Clean data" represents all the reads obtained after filtering and removal of low quality reads from the raw data (all the reads before quality filtering). Mbp, million base pair.

| Sample name | Insert size (bp) | Raw data (Mbp) | Clean data (Mbp) |
|---|---|---|---|
| Superior pool | 500 | 533 | 519 |
| Inferior pool | 500 | 532 | 518 |
| Inferior parent (Fseg25) | 500 | 520 | 506 |

Example 3

Bioinformatics Analysis

Reads obtained from each pool and from the two parents were mapped against the sequence of the reference laboratory strain S288c using SeqMan Ngen (Lasergene). The SNPs present in each pool and in the two parent strains (GS1.11-26 and Fseg25) were computed. Next, the SNPs in GS1.11-26 that were not shared by the inferior parent Fseg25 were determined, resulting in a set of specific SNPs between GS1.11-26 and Fseg25. Only these SNPs unique to the superior parent GS1.11-26 compared to the inferior parent Fseg25 were then selected from the SNP list of the superior and inferior pool. This is because SNPs (compared to S288c as reference) that are present in both parents are always present in all the segregants and are thus useless for genetic mapping. Subsequently, the variant frequency of each SNP was plotted against its chromosomal position using the statistical software R. Smoothening of the SNP frequency was performed using an algorithm Linear Mixed Model (LMM), under smoothing splines (Claesen et al., 2013). In this model, the scattered SNP variant frequency points are transformed into an average line over the length of the chromosome taking into account the sequence depth, the sequence quality and the distance between polymorphisms.

Example 4

Segregation in Diploid Segregants (Tetraploid Parent)

In order to make statistical inferences for the identification of putative QTLs, we first examined the possible biological pattern of inheritance (meiotic segregation) of polymorphisms in diploid segregants obtained from a tetraploid parent. Polymorphisms in haploid segregants obtained from a diploid parent normally follow a 2:2 segregation. Therefore, in regular PSS, the average SNP variant frequency for random segregation (locus not linked to the phenotype) is around 0.5. In this case, a statistically significant deviation of the SNP variant frequency from 0.5 indicates the presence of a putative QTL (Swinnen et al., 2012a).

On the other hand, segregation of spores from a tetraploid strain follows a more complex chromosomal inheritance than the regular 2:2 segregation manifested by haploid segregants from a diploid parent. The four meiotic spores of a tetrad made by a tetraploid parent mostly contain a diploid genome (Albertin et al., 2009). As a result, the polymorphisms in a tetraploid parent do not follow the regular 2:2 segregation in the diploid offspring. The chromosomes in an autotetraploid yeast (generated from two strains of the same species) have no preferential pairing during meiosis. This results in random bivalent pairing, formation of quadrivalents or a combination of both during meiosis (Stift et al., 2010). Since the tetraploid parent in our study was generated by crossing two strains of the same species (autotetraploid), we assumed that the meiotic spores followed tetrasomic inheritance (mendelian or random segregation). Because the effect of the quadrivalent pairing during meiosis has relatively little influence on the SNP frequency in the segregants, tetrasomic inheritance with bivalent pairing was assumed to determine the expected SNP frequency in the segregants. An example of the SNP inheritance pattern in the segregants is given in FIG. 2.

Example 5

Segregation of Homozygous SNP Nucleotide in Diploid Segregants

In case of random segregation or when the SNP nucleotide is not important for the phenotype, the SNP frequency is expected to be around 0.5 (FIG. 2). However, when the SNP base is important for the phenotype, the segregation patterns deviate from 0.5 depending on the role the gene (mutation) is playing. For example, if the homozygous SNP in FIG. 2 (GG vs TT) is responsible for the phenotype, and if both alleles are required to render the good phenotype (recessive), then, only genotype 1 is expected in the superior pool (with SNP frequency of 1). However, in a quantitative trait, where more than one loci might be involved, this particular locus might be compensated by other genes in other loci and therefore, the frequency might slightly drop below 1, but still higher than 0.5. In the inferior pool (pool of segregants that do not show the phenotype), genotypes 2 to 6, with at most one of the SNP allele, might be inherited, and the frequency of SNP base G will be around 0.4 (4/10).

Example 6

Segregation of Heterozygous SNP Nucleotide in Diploid Segregants

When a heterozygous SNP is responsible for the phenotype in the superior strain, the SNP frequency in both the superior and inferior pool is also different. For example, in FIG. 2 if the SNP base T (in black) is the responsible nucleotide variant for a dominant function (gain of function), then only the first three genotypes in FIG. 2 can be inherited in the superior pool, and the frequency of the SNP base T will be 0.5. However, since most of the SNPs in GS1.11-26 are homozygous, the influence of the heterozygous SNPs in the statistical analysis is minimal. Therefore, the frequency of the neighboring homozygous SNP G in FIG. 2, that also co-segregate with the heterozygous SNP T will have 66% inheritance (the first three genotypes in FIG. 2). In the inferior pool, only the last three genotypes that do not inherit the SNP base T from the superior parent can be represented in the pool. The neighboring homozygous SNP frequency in these three genotypes will then be about 33% (2 Gs and 4 Ts).

Example 7

Effect of Aneuploidy on SNP Variant Frequency

Another complexity of the genetic mapping with industrial strains is the presence of aneuploidy. When we analyze the whole genome sequence of the superior parent GS1.11-26 and the inferior parent Fseg25, we found that GS1.11-26 has three copies of chr IX and XVI, while Fseg25 carried three copies of chr III and chr X. As a result, the segregation of SNPs in these chromosomes is different from the one described above. In general, when the unique SNPs from the superior parent are used for the mapping (which is the case in our analysis), the presence of three copies of a chromosome in the superior parent results in an average SNP variant frequency above 0.5 during random segregation (because of over-representation of the chromosome from the superior parent). When a region is linked to the trait, the SNP variant frequency of the inferior pool drops below the average SNP frequency that is expected from random segregation (since most of the SNPs are inherited from the inferior parent). In this case, the SNP variant frequency of the superior pool will also be higher than the average. By the same principle, the presence of three sets of chromosomes in the inferior parent results in an average SNP frequency below 0.5 in a random segregation (since the SNPs present in the superior parent are used for the analysis). Linked regions might therefore show SNP frequencies above the average, which might be closer to 0.5 or higher.

Figure 3:
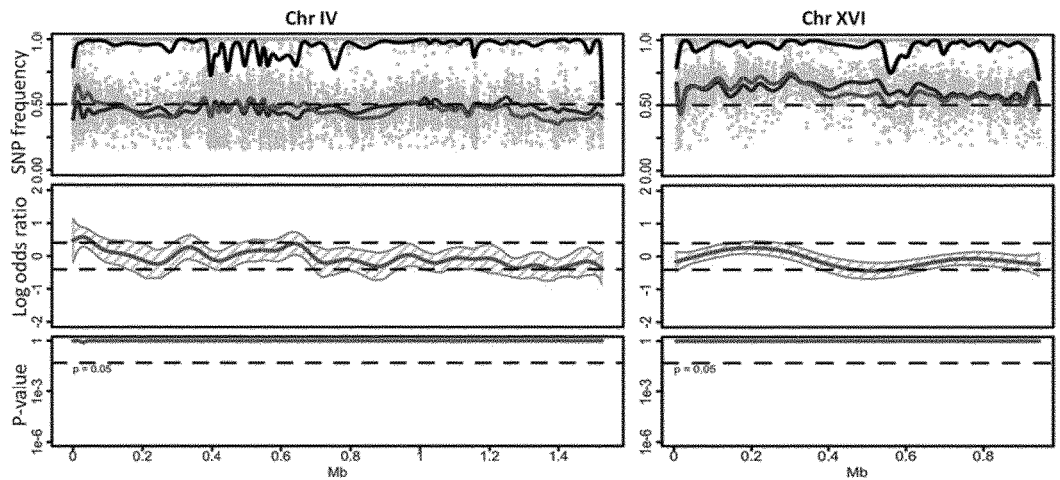
FIG. 3. Comparison between SNP variant frequency of inferior pool and superior pool in chromosome IV and chr XVI. Top panel shows the SNP variant frequency of the inferior pool and superior pool relative to the reference sequence. The dark grey and black lines in the middle represent the smoothened data for the inferior pool and superior pool, respectively. The SNP variant frequency and smoothened data of the superior parent GS1.11-26 are shown in grey circles and a black line, respectively and is used to estimate the baseline SNP variant frequency in the pools. Middle panel represents the log odds ratio (black line) along with the confidence interval (shaded regions) of the SNP variant frequency between the inferior and superior pool. Bottom panel represents the p-value for any difference between the SNP variant frequency of the inferior and superior pool (all values are close to 1, indicating no significant difference in the SNP variant frequency among the two pools.

Because of these reasons, we decided to make the statistical inferences by comparing the SNP variant frequency of the superior pool and the inferior pool, rather than the deviation of the SNP variant frequency from the normal random variant frequency of 0.5. For that purpose, the log odds ratio of the SNP variant frequencies between the superior and inferior pool was calculated along with confidence intervals. A positive log odds ratio indicates a higher SNP variant frequency in the superior pool than in the inferior pool, and therefore linkage to the superior parent. A negative log odds ratio indicates a higher SNP variant frequency in the inferior pool than in the superior pool, and therefore linkage to the inferior parent. The p-value that corresponds to the statistically significant difference in the SNP frequencies among the two pools was then calculated based on the log odds ratio. An example of a plot is shown in FIG. 3. As can be seen in the top panel for chr IV, the average SNP variant frequency is around 0.5 in both the superior and inferior pools. The middle panel shows the log odds ratio which lies within the range of ±0.4, which corresponds to an SNP variant frequency that ranges between 0.4 and 0.6. This cutoff point was selected based on previous data, in which the average SNP variant frequency for random segregation oscillates between 0.4 and 0.6 (Swinnen et al., 2012a). Another example is shown in FIG. 3 for chr XVI, where the SNP variant frequency is different from 0.5 in both the superior and inferior pool. As stated above, the superior strain GS1.11-26 has three copies of chr XVI and therefore the average SNP variant frequency was higher than 0.5 in both pools throughout that chromosome.

Example 8

Evaluation of Loci that are Linked to the Phenotype

Using the above analysis, we have identified at least 3 QTLs. In this study we investigated the two QTLs (QTL1 on chr XV and QTL2 on chr XI) that showed the strongest linkage. Since the strain GS1.11-26 is derived from its parent strain HDY.GUF5 (Demeke et al., 2013), the only possible SNPs that can explain the fast xylose fermentation rate in GS1.11-26 should be SNPs that are not shared with HDY.GUF5 (in comparison with S288c). Therefore, when comparing the genome sequence of GS1.11-26 with that of HDY.GUF5, we focused on the SNPs that were different in the two strains. There were only a limited number of polymorphisms between the two strains in these two QTLs.

Example 9

Analysis of QTL1, Chr XV

Figure 4:
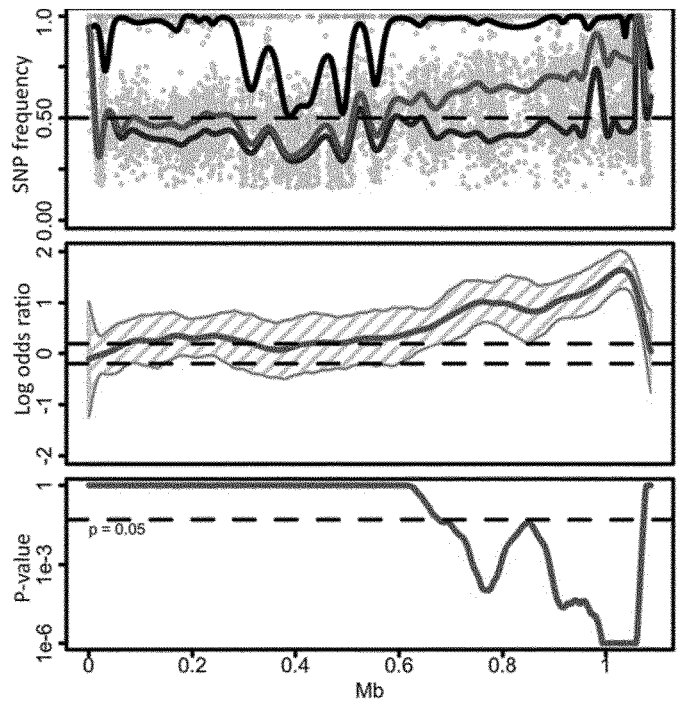
FIG. 4. Comparison between SNP variant frequency of inferior pool and superior pool in chromosome XV. Top panel shows the SNP variant frequency of the inferior pool and superior pool. The dark grey and black lines represent the smoothening data for the inferior pool and superior pool, respectively. The internal SNP variant frequency and smoothened data of the superior diploid parent GS1.11-26 is shown in grey circles and black line, respectively. Middle panel represents the log odds ratio (black line) along with the confidence interval (shaded regions) of the SNP variant frequency between the inferior and superior pool. Bottom panel represents the p-value for the difference between the SNP variant frequency of the inferior and superior pool.

The strongest linkage was found in chr XV, where the xylose metabolism gene cassette has been integrated (FIG. 4).

Figure 5:
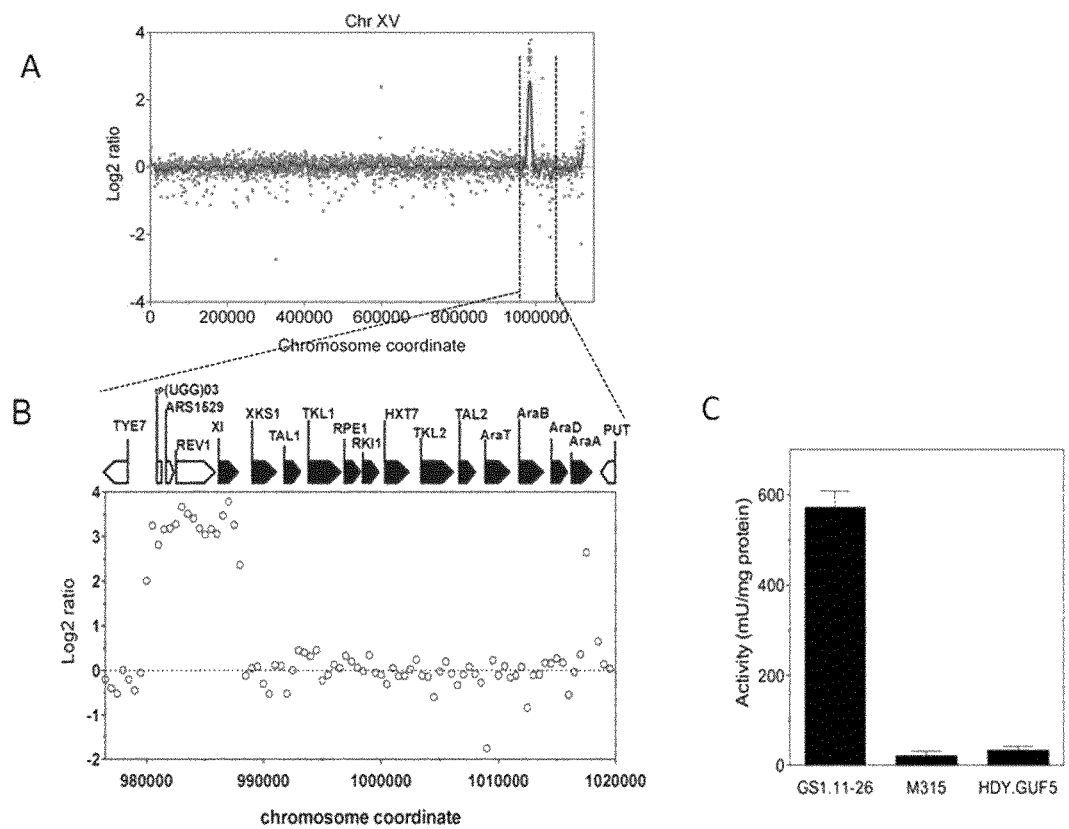
FIG. 5. Comparison of the genome sequence coverage and XI activity between the parent strain HDY.GUF5 and the evolved strain GS1.11-26 (A) Log 2 ratio depicted from whole genome sequence coverage between the evolved and the parental strain chromosome XV. Each grey circle represents the value of the log 2 ratio obtained from sequence coverage calculated for averaged sliding windows of 500 nucleotide positions. The red line indicates the smoother trend calculated by moving average values of 10,000 bp. (B) Log 2 ratio of sequence coverage between the evolved and parent strain at the PYK2 locus of chromosome XV, where the D-xylose and arabinose gene cassette has been integrated. Annotations present in the locus are indicated by bars at the top of the figure. Bars shaded in black correspond to the heterologous genes that are inserted into the chromosome, while the unshaded bars represent part of the original yeast chromosome. The coverage was computed at individual base pair level and each circle represents the average for every 100 pb. (C) Comparison of XI activity in the parent HDY.GUF5, the mutant M315 and the evolved GS1.11-26 strain. Error bars represent the standard deviation from of the mean of triplicate experiments.

In this locus, part of the integrated gene cassette, notably the xylA gene, and an upstream sequence that includes the genes REV1, a tRNA gene tP(UUG)O3 and an autonomously replicating sequence ARS1529, was amplified about 9 fold (estimated from the log 2 ratio) in the evolved strain compared to the parent strain (FIGS. 5 A and B). Since XI is the rate-limiting enzyme in D-xylose metabolism, this region was further investigated in more detail.

Increased Xylose Isomerase Activity in GS1.11-26

In order to determine if the amplification of the XylA gene also correlated with higher xylose isomerase activity, we compared the activity of xylose isomerase in the evolved GS1.11-26 strain with that in the parent HDY-GUF5 (and a mutant M315 strain obtained after the chemical mutagenesis step during the strain development (Demeke et al., 2013). The GS1.11-26 strain demonstrated much higher (about 17 fold) XI activity than the parent or the mutant M315 strain (FIG. 5 C). The high XI activity is consistent with the high copy number of xylA in the evolved strain.

Figure 6:
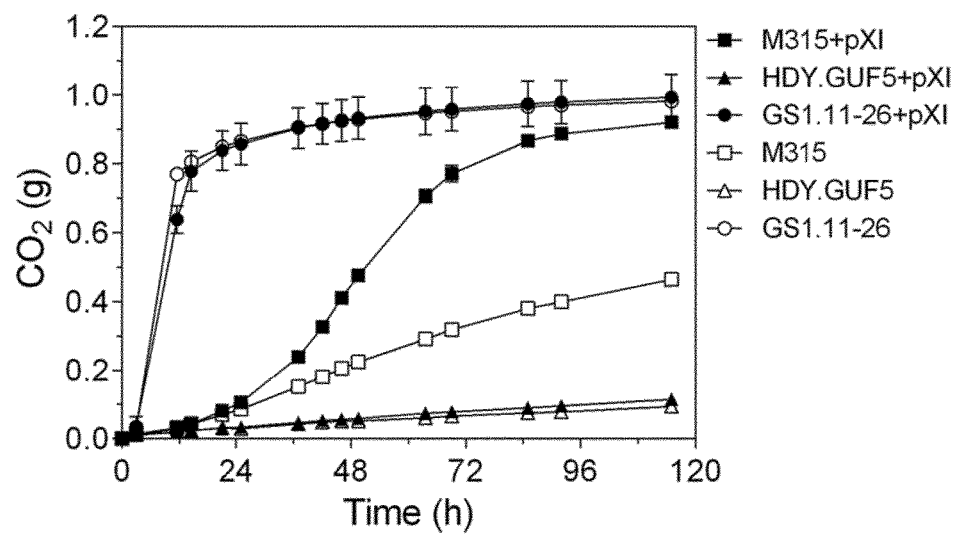
FIG. 6. Evaluation of XI over-expression on D-xylose fermentation capacity through expression of the XylA gene from a multi-copy plasmid. pXI stands for multicopy plasmid containing XylA. Only the 2μ based plasmid is shown. The ARS based plasmid gave a similar result. Each strain was inoculated into YP medium containing 40 g/L D-xylose, at an initial cell density of 1.3 gDW/L and incubated at 35° C. The $CO_2$ production was estimated from the weight loss of the total culture. Error bars represent standard error of the mean between duplicate experiments (using two independent transformants).

Amplification of xylA is not the Sole Reason for the High D-xylose Fermentation Capacity In order to determine whether amplification of the XylA gene is the only reason for the high D-xylose fermentation performance of GS1.11-26, and also whether it is still a limiting factor for D-xylose fermentation capacity in the strain, the xylA gene was over-expressed in a multicopy plasmid into the parent strain HDY-GUF5, the evolved strain GS1.11-26, and the mutant M315. When the transformants were tested for D-xylose fermentation, there was no further improvement of GS1.11-26 upon further over-expression of the xylA gene, indicating that XI might not be a limiting factor anymore in GS1.11-26 under the fermentation conditions used (FIG. 6). In addition, evaluation of several transformants of the HDY-GUF5 strain with both ARS based and 2µ based plasmids carrying the XylA gene did not bring about any notable improvement of D-xylose fermentation capacity, showing that the amplification of XylA is not the sole reason for the superior D-xylose fermentation phenotype of GS1.11-26. On the other hand, when either plasmid was transformed into the mutant strain M315, the transformants showed much higher D-xylose fermentation capacity, though not as high as GS1.11-26 (FIG. 6). This shows that M315 has one or more crucial mutations in the genome (generated by the mutagenesis step) that are essential for the superior D-xylose fermentation phenotype in combination with over-expression of XI.

In addition, other beneficial genetic changes might have accumulated during the subsequent genome shuffling and/or evolutionary engineering process. This can explain why the M315 strain, containing either the ARS based or the 2µ based XI plasmid, did not ferment D-xylose as good as the final strain GS1.11-26. However, the difference in the phenotype might also be due to the difference in the expression level of XI, since the copy number of the plasmids is unknown and may be lower than the total amplification of XylA in the genome. Therefore, the significant deviation of the SNP frequency from 0.5 in this QTL was associated to the amplified XylA-locus, which is essential for the high xylose fermentation rate and should thus be present in all the segregants.

Example 10

Analysis of QTL2, Chr XI

Figure 7:
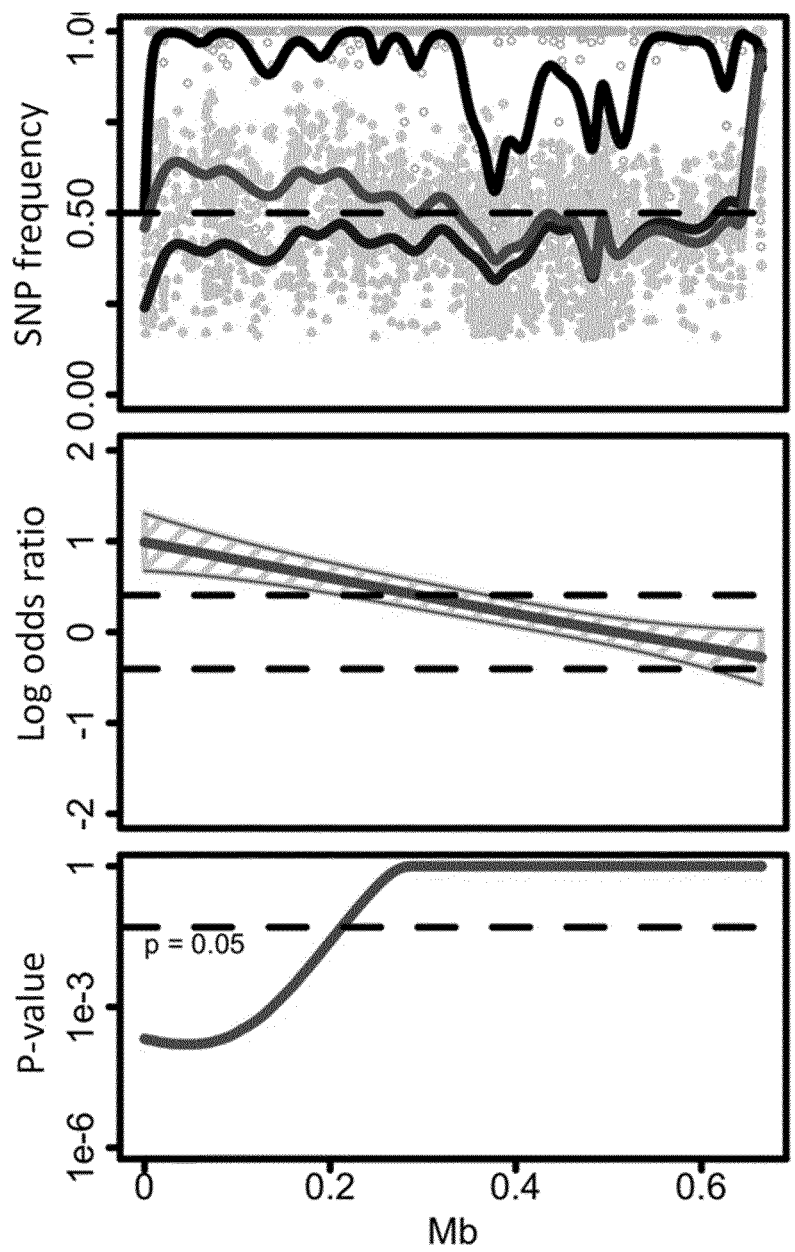
FIG. 7. Comparison between SNP variant frequency of inferior pool and superior pool for chromosome XI. Top panel shows the SNP variant frequency of the inferior pool and superior pool. The dark grey and black lines represent the smoothening data for the inferior pool and superior pool, respectively. The internal SNP variant frequency and smoothened data of the superior diploid parent GS1.11-26 is shown in grey circles and black line, respectively. Middle panel represents the log odds ratio (black line) along with the confidence interval (shaded regions) of the SNP variant frequency between the inferior and superior pool. Bottom panel represents the p-value corresponding to the difference between the SNP variant frequency of the inferior and superior pool.

The second locus with a statistically significant linkage was located on chromosome XI (FIG. 7). In this region, the average SNP variant frequency in the superior pool was about 0.6 while in the inferior pool was around 0.4. Though the SNP variant frequency in both pools was close to 0.5, the contrast between the two pools showed that the difference in the SNP frequency was statistically significant. As described above, a statistically significant deviation of the SNP variant frequency from 0.5 in the superior pool may not be as evident when evaluating diploid compared to haploid segregants. Instead, a significant difference between the SNP variant frequency of the superior and inferior pools is a better parameter to identify QTLs in diploid segregants, especially when a gain of function mutation is involved in the phenotype (see section "Segregation in diploid segregants (tetraploid parent)"). Using this approach, the first 200 kb of the chromosome showed the strongest linkage.

Figure 8:
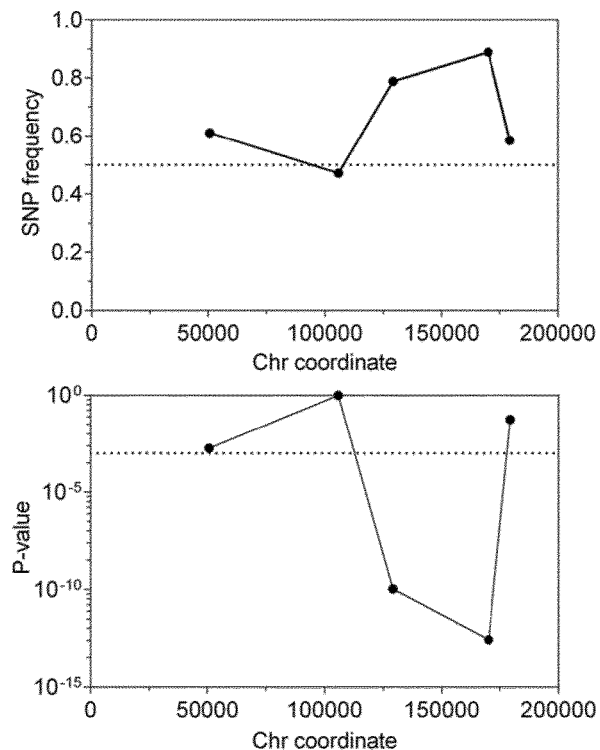
FIG. 8. SNP variant frequency (top) and p-value (bottom) for the 5 selected SNPs in the individual segregants of the superior pool. The p-value was calculated based on the deviation of the SNP frequency from 0.5.

When the polymorphisms between the parent HDY.GUF5 and the evolved strain GS1.11-26 in this locus were compared, there were only 12 SNPs that were located either within an ORF or close to an ORF (500 bp upstream and 300 bp downstream) (Table 2). To further narrow down the region, we performed fine mapping of the locus with allele specific PCR assay in the 27 individual segregants. Since all the segregants have a diploid genome (therefore, there are two possible alleles), the scoring method to determine the SNP variant frequency for individual SNPs had to be modified. We first searched for homozygous SNPs that are unique to either the superior diploid parent GS1.11-26 or the inferior diploid parent Fseg25. We then performed an allele specific PCR assay to detect only these SNPs in the individual segregants. When an individual segregant carried the SNP nucleotide from both parents, it was given a score of 1, (since it carries the SNP nucleotide only once). When it carried the SNP nucleotide from only one of the two parents (carries two times the same nucleotide), it was given a score of 2. The 27 segregants were evaluated in this way and the results allowed in reducing the strongly linked area to about 50 kb (FIG. 8).

This region contains about 24 genes, but only 5 genes had mutations unique to GS1.11-26 compared to its parent strain HDY.GUF5 (Table 3). One of the mutations is located upstream of the genes SDH1 (Crick strand) and AVT3 (Watson strand) (which might be in the promoter of both genes), and another one is a synonymous mutation in the gene MCR1. The other 3 are missense mutations in NNK1, ELF1 and SDH3.

TABLE 3

SNPs found in GS1.11-26 relative to the wild type HDYGUF5 in the QTL2 locus.
Only SNPs in an ORF or 500 bp upstream or 300 bp downstream of an ORF are shown.
SNPs that alter the amino acid sequence are shown in bold. All the SNPs were heterozygous
in the evolved strain. The function of the gene products was taken from *Saccharomyces*
Genome Database (http://www.yeastgenome.org/)

| Chr coordinate | Reference base | SNP base | Coverage | Type of mutation | Gene | Function |
| --- | --- | --- | --- | --- | --- | --- |
| 22034 | C | T | 18 | Upstream | JEN1 | Monocarboxylate/proton symporter of the plasma membrane |
| 41069 | C | T | 30 | Missense | UBA1 | Ubiquitin activating enzyme (E1) |
| 54146 | G | A | 33 | Missense | EAP1 | eIF4E-associated protein, |
| 106249 | G | A | 43 | Missense | FAS1 | Beta subunit of fatty acid synthetase |
| 119732 | C | T | 48 | Missense | ZRT3 | Vacuolar membrane zinc transporter |
| 119863 | C | T | 40 | Synonymous | ZRT3 | Vacuolar membrane zinc transporter |
| 121834 | C | T | 46 | Missense | TPO5 | Protein involved in excretion of putrescine and spermidine |
| 129894 | G | A | 21 | Missense | NNK1: | Protein kinase; implicated in proteasome function |
| 153491 | G | A | 36 | Missense | ELF1 | Transcription elongation factor that contains a conserved zinc finger domain |
| 167338 | C | T | 18 | Synonymous | MCR1 | Mitochondrial NADH-cytochrome b5 reductase, involved in ergosterol biosynthesis |
| 171522 | C | A | 32 | Upstream | SDH1/ AVT3 | SDH1 = Flavoprotein subunit of succinate Dehydrogenase: AVT3 = Amino acid Vacuolar Transport |
| 179847 | G | A | 42 | Missense | SDH3 | Subunit of both succinate dehydrogenase and of TIM22 translocase |

Figure 9:
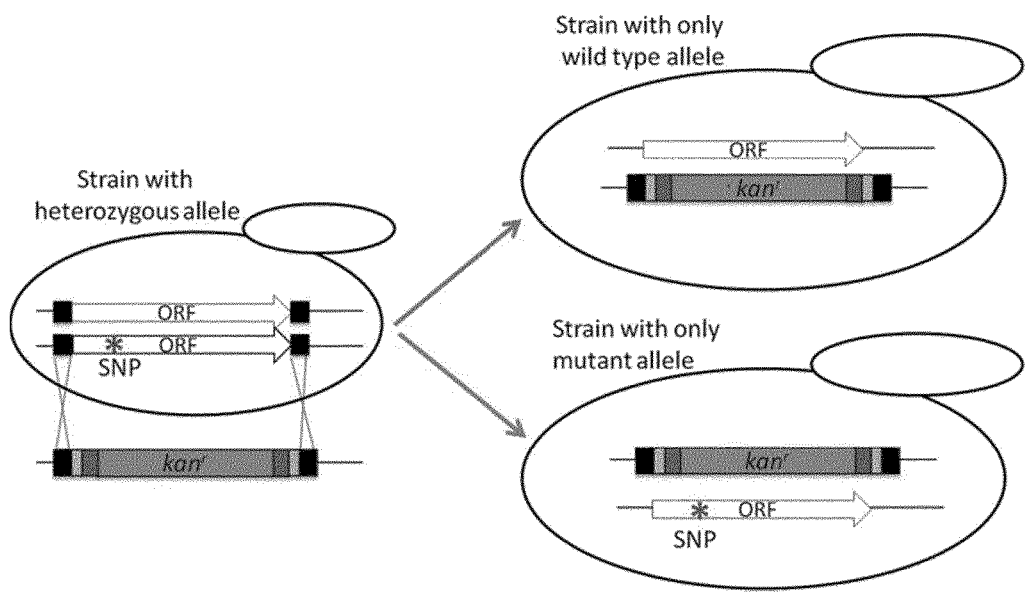
FIG. 9. Strategy used for construction of the reciprocal deletion strains with a different allele for RHA using the φC31 integration system. A strain with two heterozygous alleles was transformed with a PCR product containing a kanamycin resistance marker flanked with a homologous region (black) on either side of the ORF to be deleted. A few transformants were picked up and the region with the mutation in the gene under investigation was sequenced. Transformants with a single gene deletion and containing either the wild type allele or the mutant allele of the gene were selected for evaluation. Bars in dark grey represent the attP (left) and attB (right) sequences that are used to remove the marker using the φC31 integrase system. The green bars represent adaptors for PCR amplification of the marker.

All 5 mutations were heterozygous in the superior parent GS1.11-26 compared to the inferior parent Fse25 (which has the same genome sequence as the reference genome from S288c). We then evaluated the possible involvement of all 5 mutations by deleting either the mutant or the wild type allele in the GS1.11-26 strain. First, the ORF of SDH3, MCR1, ELF1 and NNK1, as well as the sequence between AVT3 and SDH1 (containing the SNP) were replaced by a kanamycin resistance marker. This resulted in the deletion of either the mutant or the wild type allele (FIG. 9). As a result, deletion strains that possess only the wild type allele or the mutant allele were obtained. These strains were identical with respect to their genome, except for the particular allele under study; therefore, comparison of the two strains allows to evaluate the effect of either allele. Each couple of strains with reciprocally deleted alleles was then evaluated for fermentation performance in D-xylose medium.

Figure 10:
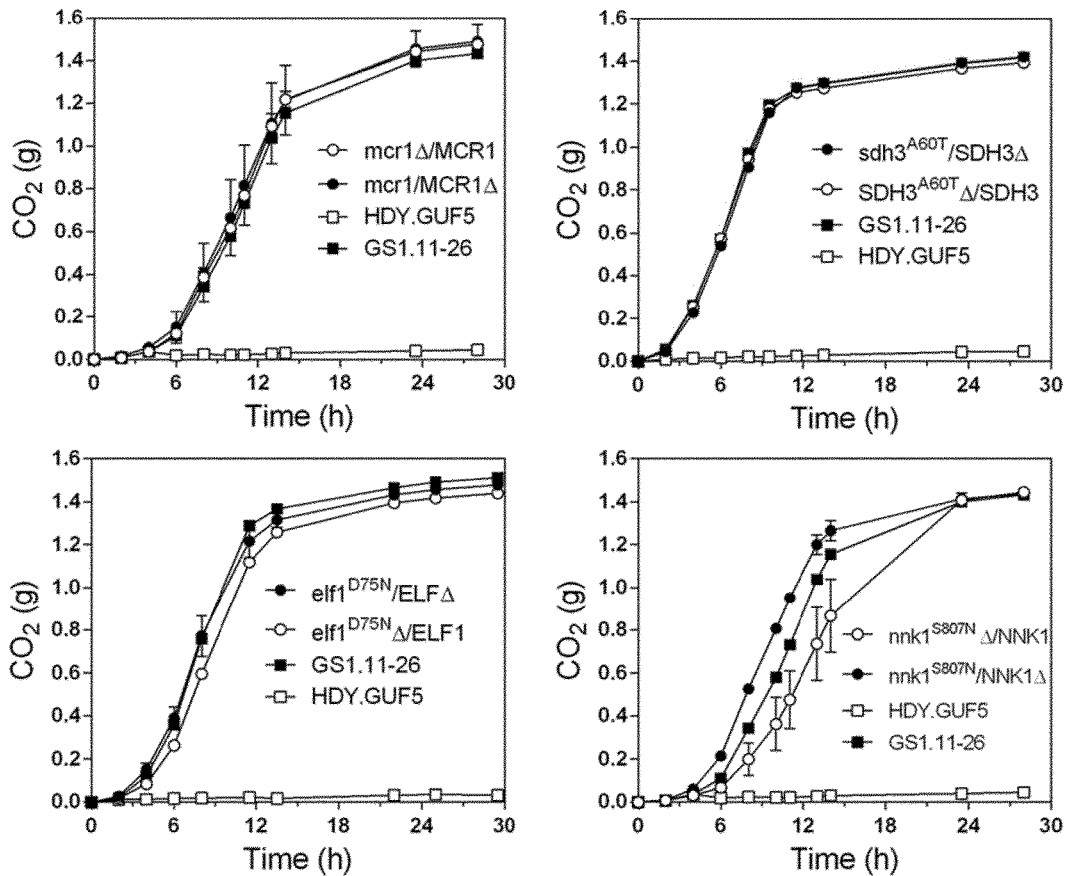
FIG. 10. D-xylose fermentation profile of strains that are reciprocally deleted for the four ORFs in the GS1.11-26 strain background. At least two independent transformants were evaluated for each gene except for ELF1, for which two transformants with a mutant allele and one transformant with a wild type allele were evaluated. Genes with the mutant allele are indicated with small letter with the amino acid change, while genes with the wild type allele are shown in capital letter. MCR1 had a synonymous mutation. GS1.11-26 carried the heterozygous alleles for all the genes tested. The GS1.11-26 strain carrying only the wild type NNK1 shows slower fermentation profile compared to the same strain carrying the mutant $nnk1^{S807N}$ allele.

As can be seen from FIG. 10 reciprocal deletion of the three genes (SDH3, MCR1 and EIF1) and the region between AVT3 and SDH1 did not result in any clear difference in the rate of D-xylose fermentation compared to the original GS1.11-26 strain. However, a very clear difference in D-xylose fermentation rate was observed among the strains that are reciprocally deleted for the NNK1 allele. The strain that carried only the wild type allele of NNK1 showed a much slower rate of fermentation compared to the strain that carried only the mutant allele (nnk1$^{S807N}$). The fermentation rate by strains carrying only the nnk1$^{S807N}$ allele of the superior parent GS1.11-26 was also slightly better than that of the original GS1.11-26 strain (that carried the two different alleles).

Figure 11:
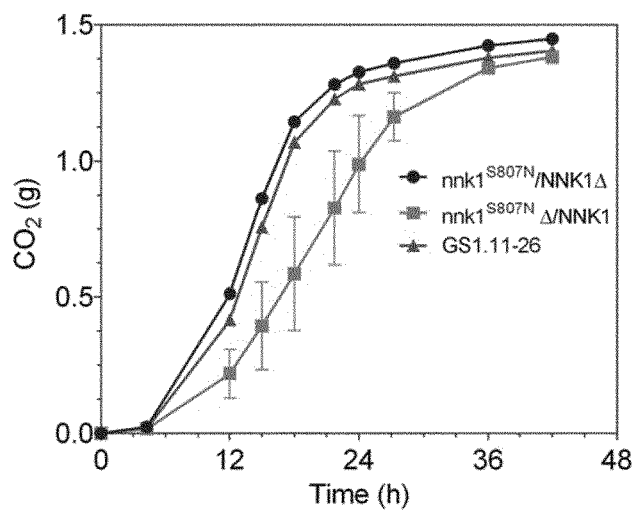
FIG. 11. Fermentation profile in YP+4% D-xylose by the GS1.11-26 and its derivatives that are reciprocally deleted for the NNK1 gene. Error bars represent standard deviation from the mean of three independent transformants. More variation was observed for the strains carrying only the wild type NNK1 allele.

To further confirm the importance of the mutation in NNK1, more strains that carry only the mutant or only the wild type allele were evaluated for fermentation performance in YP medium containing D-xylose as a carbon source. FIG. 11 shows the performance of these strains in comparison to GS1.11-26 that carried both alleles. We found similar fermentation profile as the above experiment, where the strain carrying only the mutant allele performed much better than the strain carrying only the wild type allele. In addition, the strain with mutant allele showed even better fermentation profile than the GS1.11-26, indicating that the wild type allele might have a slight negative effect in the GS1.11-26 on D-xylose fermentation rate.

Example 11

Effect of Homozygous Mutant Allele in xylose Fermentation

Figure 12:
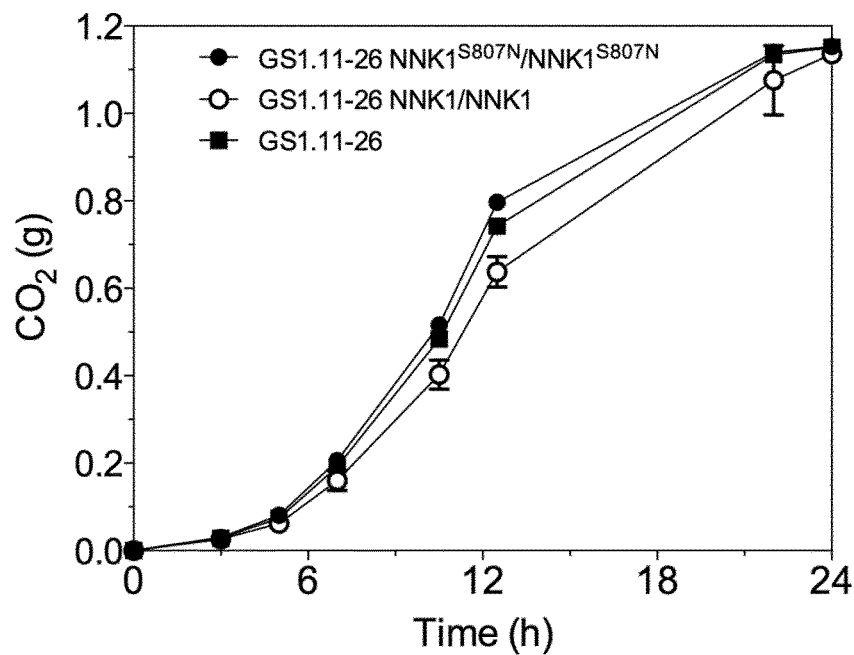
FIG. 12. Fermentation performance of strains carrying double wild type (GS1.11-26 NNK1/NNK1 and double mutant (GS1.11-26 $nnk1S^{807}$ N/$nnk1S^{807}$ N) alleles, in YP+4% xylose. The fermentation was performed in duplicates. Error bars indicate standard errors from the mean.
Figure 13:
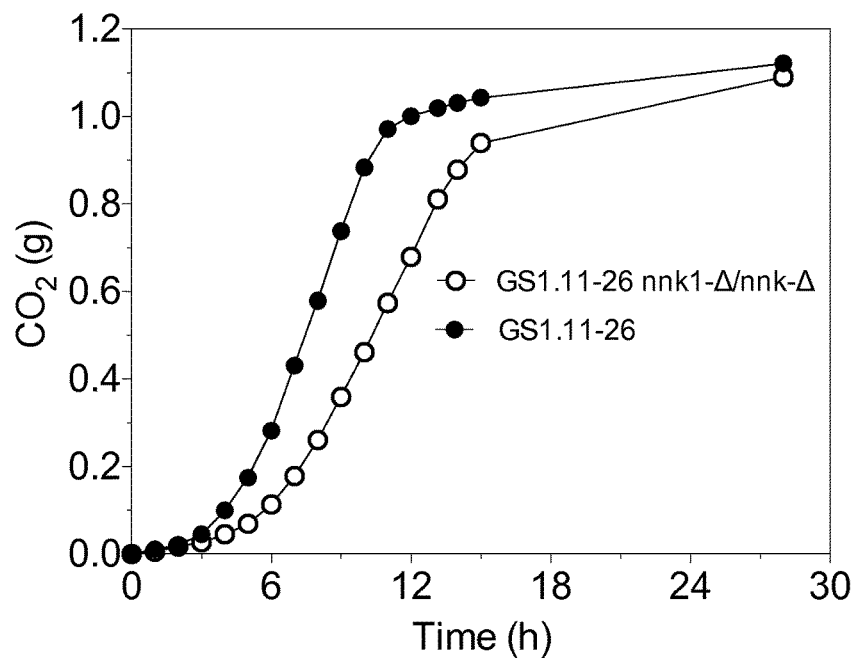
FIG. 13. Effect of double knockout of the NNK1 gene in GS1.11-26 on D-xylose fermentation capacity. Two independent double deletion strains were evaluated in YP+4% xylose, (standard errors are too small to be seen in the graph). The maximum CO2 production rate of the double deletion strains are reduced by 38% compared to the original GS1.11-26 (0.159 compared to 0.0985).

Since GS1.11-26 carried a mutant and a wild type NNK1 allele (NNK1/nnk1S$^{867}$), we evaluated the effect of two copies of either the wild type or the mutant alleles in the GS1.11-26 strain background. First we inserted a second copy of the wild type NNK1 allele into the strain GS1.11-26 NNK1/nnk1S$^{807}$ NΔ from which the mutant allele has been deleted. Similarly a second copy of the mutant nnk1S$^{807}$ allele is inserted into the strain GS1.11-26 NNK1Δ/nnk1S$^{807}$ N that already carried one mutant allele. These resulted in two identical strains that vary only in the NNK1 alleles, one carrying two copies of wild type allele (double wild type, GS1.11-26 NNK1/NNK1) and another one carrying two copies of mutant allele (double mutant, GS1.11-26 nnk1S$^{807}$ N/nnk1S$^{807}$ N). These two strains were subsequently evaluated for fermentation performance in YP+4% xylose. The results showed that the double mutant strain showed a more rapid fermentation rate compared to the double wild type strain (FIG. 12). The volumetric ethanol productivity has been 16% higher in the double mutant strain compared to the double wild type strain. Moreover, deletion of both copies of the gene severely reduced the xylose fermentation performance (FIG. 13). The volumetric ethanol productivity from xylose has been decreased by 38% in double deletion strain compared to the original strain carrying the heterozygous allele.

On the other hand no significant improvement has been observed between the double mutant strain and the strain with a single mutant allele. This indicates that mutant NNK1 allele does not have an additive effect on the D-xylose fermentation rate in the condition tested. Nevertheless, the mutation in NNK1 significantly improved the rate of D-xylose fermentation.

REFERENCES

Albertin, W., Marullo, P., Aigle, M., Bourgais, A., Bely, M., Dillmann, C., De Vienne, D., Sicard, D., 2009. Evidence for autotetraploidy associated with reproductive isolation in *Saccharomyces cerevisiae*: towards a new domesticated species. J. Evol. Biol. 22, 2157-2170.

Altschul, S. F., Madden, T. L., Schäffer, A. A., Zhang, J., Zhan, Z., Miller, W. And Lipman, D. J. (1997). Gapped BLAST and PSI-BLAST: a new generation of protein database search programs. Nucl. Acids Res. 25, 3389-3402.

Claesen, J., Clement, L., Shkedy, Z., Foulquié-Moreno, M. R., Burzykowski, T., 2013. Simultaneous Mapping of Multiple Gene Loci with Pooled Segregants. PLoS ONE 8, e55133.

Demeke, M. M., Dietz, H., Li, Y., Foulquié-Moreno, M. R., Mutturi, S., Deprez, S., Abt, T. D., Bonini, B. M., Liden, G., Dumortier, F., Verplaetse, A., Boles, E., Thevelein, J. M., 2013. Development of a D-xylose fermenting and inhibitor tolerant industrial *Saccharomyces cerevisiae* strain with high performance in lignocellulose hydrolysates using metabolic and evolutionary engineering. Biotechnol. Biofuels 6, 89.

Gietz, R. D., Schiestl, R. H., Willems, A. R., Woods, R. A., 1995. Studies on the transformation of intact yeast cells by the LiAc/SS-DNA/PEG procedure. Yeast Chichester Engl. 11, 355-360.

Hoffman, C. S., Winston, F. 1987. A ten-minute DNA preparation from yeast efficiently releases autonomous plasmids for transformation of *Escherichia coli*. Gene, 57, 267-272.

Huxley, C., Green, E. D., Dunham, I., 1990. Rapid assessment of *S. cerevisiae* mating type by PCR. Trends Genet. TIG 6, 236.

Johnston J R., 1994. Molecular genetics of yeast: A practical approach. Oxford University Press, New York.

Kersters-Hilderson, H., Callens, M., Van Opstal, O., Van-grysperre, W., De Bruyne, C. K., 1987. Kinetic characterization of d-xylose isomerases by enzymatic assays using d-sorbitol dehydrogenase. Enzyme Microb. Technol. 9, 145-148.

Kuyper, M., Toirkens, M. J., Diderich, J. A., Winkler, A. A., van Dijken, J. P., Pronk, J. T., 2005. Evolutionary engineering of mixed-sugar utilization by a xylose-fermenting *Saccharomyces cerevisiae* strain. FEMS Yeast Res. 5, 925-934.

Popolo, L., Vanoni, M., Alberghina, L., 1982. Control of the yeast cell cycle by protein synthesis. Experimental Cell Research 142,69-78.

Sambrook J, Fritsch E F, Maniatis T, 1989. Molecular cloning: a laboratory manual, 2nd. ed. Cold Spring Harbor, N. Y.

Steinmetz, L. M., Sinha, H., Richards, D. R., Spiegelman, J. I., Oefner, P. J., McCusker, J. H., Davis, R. W. 2002. Dissecting the architecture of a quantitative trait locus in yeast. Nature, 416, 326-330.

Stift, M., Reeve, R., Van TIENDEREN, P. H., 2010. Inheritance in tetraploid yeast revisited: segregation patterns and statistical power under different inheritance models. J. Evol. Biol. 23, 1570-1578.

Swinnen, S., Schaerlaekens, K., Pais, T., Claesen, J., Hubmann, G., Yang, Y., Demeke, M., Foulquié-Moreno, M. R., Goovaerts, A., Souvereyns, K., Clement, L., Dumortier, F., Thevelein, J. M., 2012a. Identification of Novel Causative Genes Determining the Complex Trait of High Ethanol Tolerance in Yeast Using Pooled-Segregant Whole-Genome Sequence Analysis. Genome Res. 22,975-984.

Swinnen, S., Thevelein, J. M., Nevoigt, E., 2012b. Genetic mapping of quantitative phenotypic traits in *Saccharomyces cerevisiae*. FEMS Yeast Res. 12,215-227.

Thompson, J. R., Register, E., Curotto, J., Kurtz, M., Kelly, R., 1998. An improved protocol for the preparation of yeast cells for transformation by electroporation. Yeast 14,565-571.

Wisselink, H. W., Toirkens, M. J., Wu, Q., Pronk, J. T., van Mans, A. J. A., 2009. Novel Evolutionary Engineering Approach for Accelerated Utilization of Glucose, Xylose, and Arabinose Mixtures by Engineered *Saccharomyces cerevisiae* Strains. Appl. Environ. Microbiol. 75,907-914.

The invention claimed is:

1. A genetically modified xylose fermenting yeast strain, comprising a mutant DNA molecule that corresponds to a mutant nitrogen network kinase 1 (NNK1) allele and encodes a mutant kinase protein carrying a mutation at position 807 of a wild type kinase protein the amino acid sequence of which is 95% identical to SEQ ID NO: 2, wherein the yeast strain is not *Saccharomyces cerevisiae* strain GS1.11-26 and wherein the mutant increases the xylose-to-ethanol fermentation rate as compared to the wild type.

2. The yeast strain according to claim 1, which has an increased fermentation rate as compared to the fermentation rate of an isogenic yeast strain not comprising said mutant DNA molecule when the fermentation is carried out under the same conditions.

3. The yeast strain according to claim 1, wherein said mutation in the protein is a serine to asparagine replacement.

4. The yeast strain according to claim 1, which is a member of a yeast genus selected from the group consisting of *Saccharomyces, Zygosaccharomyces, Brettanomyces* and *Kluyverocmyces*.

5. The yeast strain according to claim 4, which is a member of the species *Saccharomyces cerevisiae*.

6. The yeast strain according to claim 5, wherein said DNA molecule encodes a mutant protein the amino acid sequence of which is SEQ ID NO:4.

7. A process for producing ethanol comprising a step or steps in which the yeast strain of claim 1 ferments a carbohydrate to ethanol.

8. The process according to claim 7, wherein the carbohydrate comprises xylose.

9. The yeast strain according to claim 2, wherein said mutation in the protein is a serine to asparagine replacement.

10. The yeast strain according go claim 2, which is a member of a yeast genus selected from the group consisting of *Saccharomyces, Zygosaccharomyces, Brettanomyces* and *Kluyverocmyces*.

11. The yeast strain according to claim 10, which is a member of the species *Saccharomyces cerevisiae*.

12. The yeast strain according to claim 11, wherein said DNA molecule encodes a protein the amino acid sequence of which is SEQ ID NO:4.

13. A process for producing ethanol comprising fermenting a carbohydrate to ethanol employing the yeast strain of claim 2.

14. A process for producing ethanol comprising fermenting a carbohydrate to ethanol employing the yeast strain of claim 3.

15. A process for producing ethanol comprising fermenting a carbohydrate to ethanol employing the yeast strain of claim 4.

16. A process for producing ethanol comprising fermenting a carbohydrate to ethanol employing the yeast strain of claim 5.

17. A process for producing ethanol comprising fermenting a carbohydrate to ethanol employing the yeast strain of claim 11.

18. A process for producing ethanol comprising fermenting a carbohydrate to ethanol employing the yeast strain of claim 12.

\* \* \* \* \*

SEQUENCE LISTING

<160> NUMBER OF SEQ ID NOS: 7

<210> SEQ ID NO 1
<211> LENGTH: 2787
<212> TYPE: DNA
<213> ORGANISM: Saccharomyces cerevisiae

<400> SEQUENCE: 1
atgtttacgt cgcagcgaca gcttcgacaa aatgggagtc cgatgtcatc atcacgttca    60

```
tcacaacatt cctctggtac agcgtcgccg atatcagact ctccagcatc gaatcgcagc    120
tatggaagag atctacgagg cttaatggga attgatatac ctgctaacga accagctttt    180
aacagggcca atagcagtga tacaatctat ttcaggccta agaagattta caaaatggaa    240
catgagcacc catcacgatc tactttagta caactgcaga caagatcgca gccggacgat    300
gtcgcaagta gtcaagtaaa ccctgaaggc ggaaccgacg atctagagct gggcgatccg    360
tgtggcaatc aatctttata cactataggg gcggagtacg ttccagattt agactttaca    420
aagctagtga atgagtggca aaagtccacc gaggatttgt atgagttcag aagcagtgcc    480
actccgcagg tacaaatcaa agacagtgga aagggaaact acgaactttg gagctcaccg    540
gatgcaatat tgactcaaaa caaacttcga agagatagtt tttcgcaaga gaacagtgat    600
tcgttaagtc cagaagattc tattttatca agaaatttgc attctaaggt caaacccatc    660
cctctgccca gaaacagcca gcaaatattt acacccctgt ccaacttaga agcggaaagg    720
agatcctcat atacaactag tagcaacaac aatagcataa cacagaataa taaattctct    780
tttgcgaagt taaagtattc acttccaact caaagttctg cagttcctgc gtcgttcgat    840
tcaaatgctt cgtcactaaa ttttcttccg actactacat tatcgacctt atcagagcta    900
caaataagcc ccaacgatat gatggatttg attcagaagc ttcccagaaa ttttttgaac    960
ttgccgtata ctcaaaggaa aaaggtgatt atcgagcatg caccatctca tgactacaag   1020
gccatgatgt ccctagttaa gaagtttatg ttaacatctt ctagaagtaa cttttctctc   1080
gctgggtttg ccaataatgc ttcagtttcg caggccacgg ctaatgatga taacatcaat   1140
agtaggaaca cgcccaataa tagcaatgac acctacgtaa atacgcgtcc acttcaaaga   1200
tctaggcacg gttccattgc atcccaattt ttaagttctt tttcaccttc gatgacgtca   1260
atagctaaaa tgaattcgaa cccattgagt ggaagcgcag gtggcagtgc gagaccagac   1320
gataagggta tggaaatact aggtcatcgg ttgggtaaaa tcataggttt cggcgcatgg   1380
gggatcatac gggaatgctt tgatattgaa actggtgttg gtagagtgat aaaaattgtg   1440
aagttcaaag gacaccaaaa tatcaagaaa catgtgctga gagaagtagc catatggagg   1500
actttgaagc ataacagaat actcccccctt ttagattgga agcttgatga caactatgca   1560
atgtattgtt taacgaaaag aattaacgat ggtaccttat acgacttggt aatatcttgg   1620
gacgaattca aacgttcgaa gataccattt gcagagagat gcagattgac catttttta   1680 agcttacaac tattatctgc attaaagtac atgcattcca aaacgattgt tcatggtgac   1740
atcaaattag aaaactgtct gttacaaaaa gaaggtaaaa atcggattg gaaggttttc   1800 ctatgcgatt ttggaatgag ttgccacttc gatgagaagc atgtttatcg taacgatact   1860
tttgatgaaa acttgagtag tggcaacagc catagaaaga gaaaaagtat tgaacaaact   1920
aatttgataa agtatcccac aaccaatttt ttacctgacg accgaactaa tgattttgac   1980
gctagtgaaa acttaaaata ccaatttgaa aatcgaaagc atcaaccgtt tacaccaaaa   2040
ggaatggtta gctccagttc acattcatta aagcatctca atcaaccatc ctcttcttct   2100
tcttctaatc tatttcacaa gccagcctct caacctcaac cacagcatcg gagtcccttt   2160
catgggaggc acaagacaac cgattttca aacctggaac ccgaaccttc taaatatatc   2220
ggatctctgc cttacgcttc gccagaactt ctaagatact cagatgcaag acgttcaaaa   2280
tcagttgaaa tgcatatttta tgattcacca gactcctctc aatcggaaat tagcgcagca   2340
tcatcatctt cctctaattt atcttctcta tcatcctcta caaaggcgtc cgcagtcacg   2400
```

-continued

```
aattccggtg taactacaag ttcaccgtct ggttcatcga ctgatttttcc atgtattgtt    2460 tctcctttag gaccagcatc cgatatttgg gccttgggag taatgctata tacaatgtta    2520
gtaggaaaat taccctttaa tcatgagttc gaacctaggt tacgctctct gattaaagta    2580
ggcgaatttg accgattttc tttagctcag gtctgtaaat ttgacaggaa aaaaaatgaa    2640
ggaacgattg gtcaaggctt gtatgacaca gtcattggat gtttgacgat tgacttggat    2700
aagaggtgga aattgaaaag gattgaagaa gtccttcaaa acgaaatgaa cctaagcgag    2760
gccattcacg ataataatgg ctcatga                                        2787
```

<210> SEQ ID NO 2
<211> LENGTH: 928
<212> TYPE: PRT
<213> ORGANISM: Saccharomyces cerevisiae

<400> SEQUENCE: 2

```
Met Phe Thr Ser Gln Arg Gln Leu Arg Gln Asn Gly Ser Pro Met Ser
1               5                   10                  15

Ser Ser Arg Ser Ser Gln His Ser Ser Gly Thr Ala Ser Pro Ile Ser
            20                  25                  30

Asp Ser Pro Ala Ser Asn Arg Ser Tyr Gly Arg Asp Leu Arg Gly Leu
        35                  40                  45

Met Gly Ile Asp Ile Pro Ala Asn Glu Pro Ala Phe Asn Arg Ala Asn
    50                  55                  60

Ser Ser Asp Thr Ile Tyr Phe Arg Pro Lys Lys Ile Tyr Lys Met Glu
65                  70                  75                  80

His Glu His Pro Ser Arg Ser Thr Leu Val Gln Leu Thr Arg Ser
                85                  90                  95

Gln Pro Asp Asp Val Ala Ser Ser Gln Val Asn Pro Glu Gly Gly Thr
            100                 105                 110

Asp Asp Leu Glu Leu Gly Asp Pro Cys Gly Asn Gln Ser Leu Tyr Thr
        115                 120                 125

Ile Gly Ala Glu Tyr Val Pro Asp Leu Asp Phe Thr Lys Leu Val Asn
    130                 135                 140

Glu Trp Gln Lys Ser Thr Glu Asp Leu Tyr Glu Phe Arg Ser Ser Ala
145                 150                 155                 160

Thr Pro Gln Val Gln Ile Lys Asp Ser Gly Lys Gly Asn Tyr Glu Leu
                165                 170                 175

Trp Ser Ser Pro Asp Ala Ile Leu Thr Gln Asn Lys Leu Arg Arg Asp
            180                 185                 190

Ser Phe Ser Gln Glu Asn Ser Asp Ser Leu Ser Pro Glu Asp Ser Ile
        195                 200                 205

Leu Ser Arg Asn Leu His Ser Lys Val Lys Pro Ile Pro Leu Pro Arg
    210                 215                 220

Asn Ser Gln Gln Ile Phe Thr Pro Leu Ser Asn Leu Glu Ala Glu Arg
225                 230                 235                 240

Arg Ser Ser Tyr Thr Thr Ser Ser Asn Asn Asn Ser Ile Thr Gln Asn
                245                 250                 255

Asn Lys Phe Ser Phe Ala Lys Leu Lys Tyr Ser Leu Pro Thr Gln Ser
            260                 265                 270

Ser Ala Val Pro Ala Ser Phe Asp Ser Asn Ala Ser Ser Leu Asn Phe
        275                 280                 285

Leu Pro Thr Thr Thr Leu Ser Thr Leu Ser Glu Leu Gln Ile Ser Pro
    290                 295                 300
```

-continued

Asn Asp Met Met Asp Leu Ile Gln Lys Leu Pro Arg Asn Phe Leu Asn
305                 310                 315                 320

Leu Pro Tyr Thr Gln Arg Lys Val Ile Ile Glu His Ala Pro Ser
            325                 330                 335

His Asp Tyr Lys Ala Met Met Ser Leu Val Lys Lys Phe Met Leu Thr
                340                 345                 350

Ser Ser Arg Ser Asn Phe Ser Leu Ala Gly Phe Ala Asn Asn Ala Ser
            355                 360                 365

Val Ser Gln Ala Thr Ala Asn Asp Asp Asn Ile Asn Ser Arg Asn Thr
    370                 375                 380

Pro Asn Asn Ser Asn Asp Thr Tyr Val Asn Thr Arg Pro Leu Gln Arg
385                 390                 395                 400

Ser Arg His Gly Ser Ile Ala Ser Gln Phe Leu Ser Ser Phe Ser Pro
                405                 410                 415

Ser Met Thr Ser Ile Ala Lys Met Asn Ser Asn Pro Leu Ser Gly Ser
            420                 425                 430

Ala Gly Gly Ser Ala Arg Pro Asp Asp Lys Gly Met Glu Ile Leu Gly
            435                 440                 445

His Arg Leu Gly Lys Ile Gly Phe Gly Ala Trp Gly Ile Ile Arg
450                 455                 460

Glu Cys Phe Asp Ile Glu Thr Gly Val Gly Arg Val Ile Lys Ile Val
465                 470                 475                 480

Lys Phe Lys Gly His Gln Asn Ile Lys Lys His Val Leu Arg Glu Val
                485                 490                 495

Ala Ile Trp Arg Thr Leu Lys His Asn Arg Ile Leu Pro Leu Leu Asp
            500                 505                 510

Trp Lys Leu Asp Asp Asn Tyr Ala Met Tyr Cys Leu Thr Glu Arg Ile
            515                 520                 525

Asn Asp Gly Thr Leu Tyr Asp Leu Val Ile Ser Trp Asp Glu Phe Lys
530                 535                 540

Arg Ser Lys Ile Pro Phe Ala Glu Arg Cys Arg Leu Thr Ile Phe Leu
545                 550                 555                 560

Ser Leu Gln Leu Leu Ser Ala Leu Lys Tyr Met His Ser Lys Thr Ile
                565                 570                 575

Val His Gly Asp Ile Lys Leu Glu Asn Cys Leu Leu Gln Lys Glu Gly
            580                 585                 590

Lys Lys Ser Asp Trp Lys Val Phe Leu Cys Asp Phe Gly Met Ser Cys
            595                 600                 605

His Phe Asp Glu Lys His Val Tyr Arg Asn Asp Thr Phe Asp Glu Asn
610                 615                 620

Leu Ser Ser Gly Asn Ser His Arg Lys Arg Lys Ser Ile Glu Gln Thr
625                 630                 635                 640

Asn Leu Ile Lys Tyr Pro Thr Thr Asn Phe Leu Pro Asp Asp Arg Thr
                645                 650                 655

Asn Asp Phe Asp Ala Ser Glu Asn Leu Lys Tyr Gln Phe Glu Asn Arg
            660                 665                 670

Lys His Gln Pro Phe Thr Pro Lys Gly Met Val Ser Ser Ser His
            675                 680                 685

Ser Leu Lys His Leu Asn Gln Pro Ser Ser Ser Ser Ser Asn Leu
            690                 695                 700

Phe His Lys Pro Ala Ser Gln Pro Gln Pro Gln His Arg Ser Pro Phe
705                 710                 715                 720

His Gly Arg His Lys Thr Thr Asp Phe Ser Asn Leu Glu Pro Glu Pro

|  |  |  | 725 |  |  |  | 730 |  |  |  | 735 |  |
|---|---|---|---|---|---|---|---|---|---|---|---|---|
| Ser | Lys | Tyr | Ile | Gly | Ser | Leu | Pro | Tyr | Ala | Ser | Pro | Glu | Leu | Leu | Arg |
|  |  |  | 740 |  |  |  | 745 |  |  |  | 750 |  |

| Tyr | Ser | Asp | Ala | Arg | Arg | Ser | Lys | Ser | Val | Glu | Met | His | Ile | Tyr | Asp |
|  |  | 755 |  |  |  | 760 |  |  |  | 765 |  |  |  |

| Ser | Pro | Asp | Ser | Ser | Gln | Ser | Glu | Ile | Ser | Ala | Ala | Ser | Ser | Ser | Ser |
|  | 770 |  |  |  | 775 |  |  |  | 780 |  |  |  |  |

| Ser | Asn | Leu | Ser | Ser | Leu | Ser | Ser | Ser | Thr | Lys | Ala | Ser | Ala | Val | Thr |
| 785 |  |  |  | 790 |  |  |  | 795 |  |  |  | 800 |

| Asn | Ser | Gly | Val | Thr | Thr | Ser | Ser | Pro | Ser | Gly | Ser | Ser | Thr | Asp | Phe |
|  |  |  |  | 805 |  |  |  | 810 |  |  |  | 815 |

| Pro | Cys | Ile | Val | Ser | Pro | Leu | Gly | Pro | Ala | Ser | Asp | Ile | Trp | Ala | Leu |
|  |  |  | 820 |  |  |  | 825 |  |  |  | 830 |  |

| Gly | Val | Met | Leu | Tyr | Thr | Met | Leu | Val | Gly | Lys | Leu | Pro | Phe | Asn | His |
|  |  |  | 835 |  |  |  | 840 |  |  |  | 845 |  |

| Glu | Phe | Glu | Pro | Arg | Leu | Arg | Ser | Leu | Ile | Lys | Val | Gly | Glu | Phe | Asp |
|  | 850 |  |  |  | 855 |  |  |  | 860 |  |  |  |

| Arg | Phe | Ser | Leu | Ala | Gln | Val | Cys | Lys | Phe | Asp | Arg | Lys | Lys | Asn | Glu |
| 865 |  |  |  | 870 |  |  |  | 875 |  |  |  | 880 |

| Gly | Thr | Ile | Gly | Gln | Gly | Leu | Tyr | Asp | Thr | Val | Ile | Gly | Cys | Leu | Thr |
|  |  |  |  | 885 |  |  |  | 890 |  |  |  | 895 |

| Ile | Asp | Leu | Asp | Lys | Arg | Trp | Lys | Leu | Lys | Arg | Ile | Glu | Glu | Val | Leu |
|  |  |  | 900 |  |  |  | 905 |  |  |  | 910 |  |

| Gln | Asn | Glu | Met | Asn | Leu | Ser | Glu | Ala | Ile | His | Asp | Asn | Asn | Gly | Ser |
|  |  |  | 915 |  |  |  | 920 |  |  |  | 925 |

<210> SEQ ID NO 3
<211> LENGTH: 2787
<212> TYPE: DNA
<213> ORGANISM: Saccharomyces cerevisiae

<400> SEQUENCE: 3

| atgtttacgt cgcagcgaca gcttcgacaa atgggagtc cgatgtcatc atcacgttca | 60 |
| tcacaacatt cctctggtac agcgtcgccg atatcgact ctccagcatc gaatcgcagc | 120 |
| tatggaagag atctacgagg cttaatggga attgatatac ctgctaacga accagctttt | 180 |
| aacagggcca atagcagtga tacaatctat ttcaggccta agaagattta caaaatggaa | 240 |
| catgagcacc catcacgatc tactttagta caactgcaga caagatcgca gccggacgat | 300 |
| gtcgcaagta gtcaagtaaa ccctgaaggc ggaaccgacg atctagagct gggcgatccg | 360 |
| tgtggcaatc aatctttata cactataggg gcggagtacg ttccagattt agactttaca | 420 |
| aagctagtga atgagtggca aaagtccacc gaggatttgt atgagttcag aagcagtgcc | 480 |
| actccgcagg tacaaatcaa agacagtgga aagggaaact acgaactttg gagctcaccg | 540 |
| gatgcaatat tgactcaaaa caacttcga agagatagtt tttcgcaaga gaacagtgat | 600 |
| tcgttaagtc cagaagattc tatttttatca agaaatttgc attctaaggt caaacccatc | 660 |
| cctctgccca gaaacagcca gcaaatattt caccccctgt ccaacttaga agcggaaagg | 720 |
| agatcctcat atacaactag tagcaacaac aatagcataa cacagaataa taaattctct | 780 |
| tttgcgaagt taagtattc acttccaact caaagttctg cagttcctgc gtcgttcgat | 840 |
| tcaaatgctt cgtcactaaa ttttcttccg actactacat tatcgacctt atcagagcta | 900 |
| caaataagcc ccaacgatat gatggatttg attcagaagc ttcccagaaa tttttttgaac | 960 |
| ttgccgtata ctcaaaggaa aaggtgatt atcgagcatg caccatctca tgactacaag | 1020 |

```
gccatgatgt ccctagttaa gaagtttatg ttaacatctt ctagaagtaa cttttctctc    1080
gctgggtttg ccaataatgc ttcagtttcg caggccacgg ctaatgatga aacatcaat    1140 agtaggaaca cgcccaataa tagcaatgac acctacgtaa atacgcgtcc acttcaaaga    1200
tctaggcacg gttccattgc atcccaattt ttaagttctt tttcaccttc gatgacgtca    1260
atagctaaaa tgaattcgaa cccattgagt ggaagcgcag gtggcagtgc gagaccagac    1320
gataagggta tggaaatact aggtcatcgg ttgggtaaaa tcataggttt cggcgcatgg    1380
gggatcatac gggaatgctt tgatattgaa actggtgttg gtagagtgat aaaaattgtg    1440
aagttcaaag acaccaaaa tatcaagaaa catgtgctga gagaagtagc catatggagg     1500
actttgaagc ataacagaat actccccctt ttagattgga agcttgatga caactatgca    1560
atgtattgtt taacggaaag aattaacgat ggtaccttat acgacttggt aatatcttgg    1620
gacgaattca aacgttcgaa gataccattt gcagagagat gcagattgac catttttta    1680 agcttacaac tattatctgc attaaagtac atgcattcca aaacgattgt tcatggtgac    1740
atcaaattag aaaactgtct gttacaaaaa gaaggtaaaa aatcggattg aaggttttc    1800 ctatgcgatt ttggaatgag ttgccacttc gatgagaagc atgtttatcg taacgatact    1860
tttgatgaaa acttgagtag tggcaacagc catagaaaga gaaaaagtat tgaacaaact    1920
aatttgataa agtatcccac aaccaattt ttacctgacg accgaactaa tgattttgac    1980
gctagtgaaa acttaaaata ccaatttgaa atcgaaagc atcaaccgtt tacaccaaaa    2040
ggaatggtta gctccagttc acattcatta aagcatctca atcaaccatc ctcttcttct    2100
tcttctaatc tatttcacaa gccagcctct caacctcaac cacagcatcg gagtcccttt    2160
catgggaggc acaagacaac cgattttca aacctggaac ccgaaccttc taaatatatc    2220
ggatctctgc cttacgcttc gccagaactt ctaagatact cagatgcaag acgttcaaaa    2280
tcagttgaaa tgcatattta tgattcacca gactcctctc aatcggaaat tagcgcagca    2340
tcatcatctt cctctaattt atcttctcta tcatcctcta caaaggcgtc cgcagtcacg    2400
aattccggtg taactacaaa ttcaccgtct ggttcatcga ctgatttcc atgtattgtt    2460 tctcctttag accagcatc cgatatttgg gccttgggag taatgctata tcaatgtta    2520 gtaggaaaat tacccttaa tcatgagttc gaacctaggt tacgctctct gattaaagta    2580
ggcgaatttg accgattttc tttagctcag gtctgtaaat ttgacaggaa aaaaaatgaa    2640
ggaacgattg gtcaaggctt gtatgacaca gtcattggat gtttgacgat tgacttggat    2700
aagaggtgga aattgaaaag gattgaagaa gtccttcaaa acgaaatgaa cctaagcgag    2760
gccattcacg ataataatgg ctcatga                                         2787
```

<210> SEQ ID NO 4
<211> LENGTH: 928
<212> TYPE: PRT
<213> ORGANISM: Saccharomyces cerevisiae

<400> SEQUENCE: 4

```
Met Phe Thr Ser Gln Arg Gln Leu Arg Gln Asn Gly Ser Pro Met Ser
1               5                   10                  15

Ser Ser Arg Ser Ser Gln His Ser Ser Gly Thr Ala Ser Pro Ile Ser
            20                  25                  30

Asp Ser Pro Ala Ser Asn Arg Ser Tyr Gly Arg Asp Leu Arg Gly Leu
        35                  40                  45

Met Gly Ile Asp Ile Pro Ala Asn Glu Pro Ala Phe Asn Arg Ala Asn
```

```
                50              55              60
Ser Ser Asp Thr Ile Tyr Phe Arg Pro Lys Lys Ile Tyr Lys Met Glu
 65                  70                  75                  80

His Glu His Pro Ser Arg Ser Thr Leu Val Gln Leu Gln Thr Arg Ser
                     85                  90                  95

Gln Pro Asp Asp Val Ala Ser Ser Gln Val Asn Pro Glu Gly Gly Thr
                100                 105                 110

Asp Asp Leu Glu Leu Gly Asp Pro Cys Gly Asn Gln Ser Leu Tyr Thr
                115                 120                 125

Ile Gly Ala Glu Tyr Val Pro Asp Leu Asp Phe Thr Lys Leu Val Asn
                130                 135                 140

Glu Trp Gln Lys Ser Thr Glu Asp Leu Tyr Glu Phe Arg Ser Ser Ala
145                 150                 155                 160

Thr Pro Gln Val Gln Ile Lys Asp Ser Gly Lys Gly Asn Tyr Glu Leu
                165                 170                 175

Trp Ser Ser Pro Asp Ala Ile Leu Thr Gln Asn Lys Leu Arg Arg Asp
                180                 185                 190

Ser Phe Ser Gln Glu Asn Ser Asp Ser Leu Ser Pro Glu Asp Ser Ile
                195                 200                 205

Leu Ser Arg Asn Leu His Ser Lys Val Lys Pro Ile Pro Leu Pro Arg
210                 215                 220

Asn Ser Gln Gln Ile Phe Thr Pro Leu Ser Asn Leu Glu Ala Glu Arg
225                 230                 235                 240

Arg Ser Ser Tyr Thr Thr Ser Ser Asn Asn Asn Ser Ile Thr Gln Asn
                245                 250                 255

Asn Lys Phe Ser Phe Ala Lys Leu Lys Tyr Ser Leu Pro Thr Gln Ser
                260                 265                 270

Ser Ala Val Pro Ala Ser Phe Asp Ser Asn Ala Ser Ser Leu Asn Phe
                275                 280                 285

Leu Pro Thr Thr Thr Leu Ser Thr Leu Ser Glu Leu Gln Ile Ser Pro
                290                 295                 300

Asn Asp Met Met Asp Leu Ile Gln Lys Leu Pro Arg Asn Phe Leu Asn
305                 310                 315                 320

Leu Pro Tyr Thr Gln Arg Lys Lys Val Ile Glu His Ala Pro Ser
                325                 330                 335

His Asp Tyr Lys Ala Met Met Ser Leu Val Lys Lys Phe Met Leu Thr
                340                 345                 350

Ser Ser Arg Ser Asn Phe Ser Leu Ala Gly Phe Ala Asn Asn Ala Ser
                355                 360                 365

Val Ser Gln Ala Thr Ala Asn Asp Asp Asn Ile Asn Ser Arg Asn Thr
                370                 375                 380

Pro Asn Asn Ser Asn Asp Thr Tyr Val Asn Thr Arg Pro Leu Gln Arg
385                 390                 395                 400

Ser Arg His Gly Ser Ile Ala Ser Gln Phe Leu Ser Ser Phe Ser Pro
                405                 410                 415

Ser Met Thr Ser Ile Ala Lys Met Asn Ser Asn Pro Leu Ser Gly Ser
                420                 425                 430

Ala Gly Gly Ser Ala Arg Pro Asp Asp Lys Gly Met Glu Ile Leu Gly
                435                 440                 445

His Arg Leu Gly Lys Ile Ile Gly Phe Gly Ala Trp Gly Ile Ile Arg
                450                 455                 460

Glu Cys Phe Asp Ile Glu Thr Gly Val Gly Arg Val Ile Lys Ile Val
465                 470                 475                 480
```

-continued

```
Lys Phe Lys Gly His Gln Asn Ile Lys Lys His Val Leu Arg Glu Val
            485                 490                 495
Ala Ile Trp Arg Thr Leu Lys His Asn Arg Ile Leu Pro Leu Leu Asp
            500                 505                 510
Trp Lys Leu Asp Asp Asn Tyr Ala Met Tyr Cys Leu Thr Glu Arg Ile
            515                 520                 525
Asn Asp Gly Thr Leu Tyr Asp Leu Val Ile Ser Trp Asp Glu Phe Lys
        530                 535                 540
Arg Ser Lys Ile Pro Phe Ala Glu Arg Cys Arg Leu Thr Ile Phe Leu
545                 550                 555                 560
Ser Leu Gln Leu Leu Ser Ala Leu Lys Tyr Met His Ser Lys Thr Ile
            565                 570                 575
Val His Gly Asp Ile Lys Leu Glu Asn Cys Leu Leu Gln Lys Glu Gly
            580                 585                 590
Lys Lys Ser Asp Trp Lys Val Phe Leu Cys Asp Phe Gly Met Ser Cys
        595                 600                 605
His Phe Asp Glu Lys His Val Tyr Arg Asn Asp Thr Phe Asp Glu Asn
        610                 615                 620
Leu Ser Ser Gly Asn Ser His Arg Lys Arg Lys Ser Ile Glu Gln Thr
625                 630                 635                 640
Asn Leu Ile Lys Tyr Pro Thr Thr Asn Phe Leu Pro Asp Asp Arg Thr
            645                 650                 655
Asn Asp Phe Asp Ala Ser Glu Asn Leu Lys Tyr Gln Phe Glu Asn Arg
            660                 665                 670
Lys His Gln Pro Phe Thr Pro Lys Gly Met Val Ser Ser Ser Ser His
            675                 680                 685
Ser Leu Lys His Leu Asn Gln Pro Ser Ser Ser Ser Ser Asn Leu
            690                 695                 700
Phe His Lys Pro Ala Ser Gln Pro Gln Pro Gln His Arg Ser Pro Phe
705                 710                 715                 720
His Gly Arg His Lys Thr Thr Asp Phe Ser Asn Leu Glu Pro Glu Pro
            725                 730                 735
Ser Lys Tyr Ile Gly Ser Leu Pro Tyr Ala Ser Pro Glu Leu Leu Arg
            740                 745                 750
Tyr Ser Asp Ala Arg Arg Ser Lys Ser Val Glu Met His Ile Tyr Asp
            755                 760                 765
Ser Pro Asp Ser Ser Gln Ser Glu Ile Ser Ala Ala Ser Ser Ser Ser
        770                 775                 780
Ser Asn Leu Ser Ser Leu Ser Ser Thr Lys Ala Ser Ala Val Thr
785                 790                 795                 800
Asn Ser Gly Val Thr Thr Asn Ser Pro Ser Gly Ser Ser Thr Asp Phe
            805                 810                 815
Pro Cys Ile Val Ser Pro Leu Gly Pro Ala Ser Asp Ile Trp Ala Leu
            820                 825                 830
Gly Val Met Leu Tyr Thr Met Leu Val Gly Lys Leu Pro Phe Asn His
            835                 840                 845
Glu Phe Glu Pro Arg Leu Arg Ser Leu Ile Lys Val Gly Glu Phe Asp
            850                 855                 860
Arg Phe Ser Leu Ala Gln Val Cys Lys Phe Asp Arg Lys Lys Asn Glu
865                 870                 875                 880
Gly Thr Ile Gly Gln Gly Leu Tyr Asp Thr Val Ile Gly Cys Leu Thr
            885                 890                 895
```

```
Ile Asp Leu Asp Lys Arg Trp Lys Leu Lys Arg Ile Glu Glu Val Leu
            900                 905                 910

Gln Asn Glu Met Asn Leu Ser Glu Ala Ile His Asp Asn Asn Gly Ser
        915                 920                 925

<210> SEQ ID NO 5
<211> LENGTH: 18
<212> TYPE: DNA
<213> ORGANISM: Saccharomyces cerevisiae

<400> SEQUENCE: 5
acgagagcta cctaagtc                                               18

<210> SEQ ID NO 6
<211> LENGTH: 18
<212> TYPE: DNA
<213> ORGANISM: Saccharomyces cerevisiae

<400> SEQUENCE: 6
acgagagcta ccgaagtc                                               18

<210> SEQ ID NO 7
<211> LENGTH: 18
<212> TYPE: DNA
<213> ORGANISM: Saccharomyces cerevisiae

<400> SEQUENCE: 7
acgatagcta ccgaagtc                                               18
```